United States Patent
Reddy

(10) Patent No.: US 11,077,052 B1
(45) Date of Patent: Aug. 3, 2021

(54) SELECTED MULTI-PHASE TREATMENT FOR CORONAVIRUS RESPIRATORY INFECTIONS

(71) Applicant: Malireddy S. Reddy, Cherry Hills Village, CO (US)

(72) Inventor: Malireddy S. Reddy, Cherry Hills Village, CO (US)

(*) Notice: Subject to any disclaimer, the term of this patent is extended or adjusted under 35 U.S.C. 154(b) by 0 days.

(21) Appl. No.: 17/016,300

(22) Filed: Sep. 9, 2020

(51) Int. Cl.
| | |
|---|---|
| *A61K 9/00* | (2006.01) |
| *A61K 36/53* | (2006.01) |
| *A61K 47/22* | (2006.01) |
| *A61K 47/42* | (2017.01) |
| *A61P 31/14* | (2006.01) |
| *A61K 9/127* | (2006.01) |
| *A61K 31/05* | (2006.01) |
| *A61K 35/742* | (2015.01) |
| *A61K 35/745* | (2015.01) |
| *A61K 35/747* | (2015.01) |
| *A61K 35/744* | (2015.01) |
| *A61K 35/741* | (2015.01) |
| *A61K 36/064* | (2006.01) |
| *A61K 36/61* | (2006.01) |
| *A61K 36/9066* | (2006.01) |
| *A61K 47/02* | (2006.01) |

(52) U.S. Cl.
CPC ............ *A61K 9/0043* (2013.01); *A61K 9/127* (2013.01); *A61K 31/05* (2013.01); *A61K 35/741* (2013.01); *A61K 35/742* (2013.01); *A61K 35/744* (2013.01); *A61K 35/745* (2013.01); *A61K 35/747* (2013.01); *A61K 36/064* (2013.01); *A61K 36/53* (2013.01); *A61K 36/61* (2013.01); *A61K 36/9066* (2013.01); *A61K 47/02* (2013.01); *A61K 47/22* (2013.01); *A61K 47/42* (2013.01); *A61P 31/14* (2018.01)

(58) Field of Classification Search
None
See application file for complete search history.

(56) References Cited

U.S. PATENT DOCUMENTS

| | | | |
|---|---|---|---|
| 7,495,011 B2 | 2/2009 | Fujii | |
| 7,544,712 B1 | 6/2009 | Hsu | |
| 10,682,368 B2 | 6/2020 | Perron | |
| 2014/0079773 A1* | 3/2014 | Heath | A61K 31/485 424/450 |
| 2019/0328802 A1* | 10/2019 | Fein | A61K 35/747 |

FOREIGN PATENT DOCUMENTS

| | | | |
|---|---|---|---|
| CN | 110122564 A | * | 8/2019 |
| CN | 111500615 A | * | 8/2020 |
| IN | 202041019249 A | * | 5/2020 |
| JP | 2008013543 A | * | 1/2008 |

OTHER PUBLICATIONS

Costiniuk (Cytokine and Growth Factor Reviews (May 2020), vol. 53, pp. 63-65).*
Lakshmi (World Journal of Pharmaceutical Research (Jul. 2020), vol. 9, No. 7, pp. 712-731).*
Li (Frontiers in Microbiology (Aug. 2020), vol. 11, article 1794).*
Michienzi (Drugs in Context (May 7, 2020), vol. 9, pp. 1-29).*
Shi (Science (May 2020), vol. 368, pp. 1016-1020).*

* cited by examiner

*Primary Examiner* — Susan Hoffman
(74) *Attorney, Agent, or Firm* — Kyle W. Rost

(57) ABSTRACT

A multi-phase treatment of a respiratory disease in which one treatment is a lysing defense by applying inhibitory agents to respiratory passages. Application may be by nasal irrigant, oral gargling mouthwash, or smelling salt. Another treatment is an immune system suppressing defense by providing a liposome-based countermeasure to excess activity of the host immune system during COVID-19 infection. The liposome increases bio-activity of probiotics, probiotics-produced therapeutic peptides, bio-peptides, and antioxidant level in the blood with a sustained massive dose of antioxidants to counteract excess oxidation produced by excess activity of the host immune system, when administered through oral route.

16 Claims, 1 Drawing Sheet

SELECTED MULTI-PHASE TREATMENT FOR CORONAVIRUS RESPIRATORY INFECTIONS

BACKGROUND OF THE INVENTION

Technical Field

This invention relates to a drug or treatment that is a bio-affecting and body treating composition. The treatment is for inactivation of a coronavirus, with the coronavirus SARS-CoV-2 being a specific target due to its being the cause of the COVID-19 disease, which currently is regarded as a pandemic. The treatment encompasses a four-prong approach involving a novel nasal irrigation system, mouthwash with gargling, a nasal inhalator composition in a cartridge, and a nutritional therapeutic liposomal probiotic composition to be consumed orally, to prevent or cure the COVID-19 infection. In addition, the invention has broad application to prevent or cure other viral infections, coronavirus infections including but not limited to the RNA viruses belonging to influenza group of viruses, bacteria, yeast and mold infections involving mainly the pulmonary system, and other satellite secondary infections involving the other parts of the body. It has been accomplished through the involvement of multiple mixed strain probiotics along with their growth end products (immunomodulins), potentiated antioxidants, concentrated herbal supplements, food grade surfactants, and yeast and mold inhibitors, in the form of liposomes.

Description of the Related Art Including Information Disclosed Under 37 CFR 1.97 and 37 CFR 1.98

The coronavirus SARS-CoV-2 is an RNA virus. Reportedly, this virus first erupted in Wuhan, China in November 2019. The disease caused by this virus is called COVID-19 (signifying a coronavirus disease that erupted in the year 2019) according to the World Health Organization. The official name given to this virus is SARS-CoV-2 by the International Committee on Taxonomy of Viruses.

The COVID-19 virus has been transmitted from bats to intermediate animals and finally to humans. This is zoonotic virus meaning transmitted from animal to humans. If we go into history, in early 2003 SARS (Severe Acute Respiratory Syndrome) virus came from bats to civets to humans. SARS coronavirus caused severe respiratory illness. It was first reported in Asia in 2003, although it came into existence in 2002. SARS quickly spread to 26 countries, and it was contained in 4 months. More than 8,000 people fell ill from SARS and 774 died. There have been no reported cases on SARS since 2004.

In 2012, MERS (Middle East Respiratory Syndrome), which is also caused by a coronavirus, emerged in Saudi Arabia, and quickly spread to 27 countries with 2,519 confirmed infections and 866 deaths. It also originated from bats, then spread to camels and finally to humans. MERS virus is enveloped, positive sense, and has single stranded RNA.

After the current coronavirus SARS-CoV-2 infection was first reported in Wuhan, China, the World Health Organization (WHO), in January 2020, announced it as an outbreak of unknown cause. By the end of January, WHO had declared COVID-19 to be a public health emergency of international concern. On February 11th, WHO officially named infection of SARS-CoV-2 virus as COVID-19. On Mar. 11, 2020 WHO declared COVID-19 as a pandemic. As of the second week of August 2020, COVID-19 has spread to 210 countries infecting over 20.4 million people and killing over 745,000 people worldwide. It continues to spread at a rapid pace. All three of these coronaviruses have emerged since the turn of the century and have caused severe respiratory syndrome. SARS and MERS have exhibited significantly higher mortality rates than COVID-19. Although the fatality rate is lower with COVID-19, the number of deaths far outweighs that from SARS or MERS. SARS totally disappeared in the last decade, yet MERS remains an ongoing public health concern of minor significance.

The COVID-19 virus spreads through contact and infects people rather quickly. It has spread all over the world in a short time. There is no vaccine for COVID-19 currently since it is a relatively new virus. Available treatment of infected patients is minimal, such as supplying supplemental oxygen to offset restricted breathing, and immunosuppressant can be administered not so much to treat the virus itself as to decrease overstimulation of the patient's immune system. Thus as a fallback in view of limited treatment options, a major effort has been directed to preventing human acquisition of the disease, with recommendations that the public engage in frequent hand washing, avoid touching oneself at entrance points to the respiratory system, and wear respiratory masks. Precautionary measures undertaken by the entire world to contain COVID-19 virus are lockdowns and maintaining at least minimum distance between individuals. Currently several pharmaceutical and biotech companies are working to come up with either a vaccine or a therapeutic drug to cure COVID-19. Expert projections are that the timeframe needed to develop a vaccine, including necessary time to establish safety and efficacy, likely is a minimum of eighteen months. Even in this timeframe, there is no assurance of success; and even the success of a vaccine may be inadequate to prevent disease caused by mutants of the virus.

The coronavirus, as the name implies, looks like "corona" or halo when viewed under electron microscope. It has four types of proteins i.e. S-protein (spike), M-protein (membrane), E-protein (envelope) and N-protein (nucleocapsid). It has an envelope, which is made of fat (lipid), upon which the corona type spike proteins appear. Underneath the fatty envelops lies the RNA which is enveloped by a capsid.

According to a mechanism of infection, the COVID-19 virus enters the respiratory tract and makes contact with lung cells. The S-protein (spike) of the virus contacts a host cell at a receptor site (ACE-2) on the epithelial cells of the lung. The S-protein divides into two types of SP-1 and SP-2. SP-2 helps the virus to integrate with the host cell membrane and thus the virus makes entry into the cell. Inside the human cell, the viral RNA can make its progress through several biochemical or molecular mechanisms. They are as follows: The COVID-19 viral RNA can behave like MRNA (positive sense) and make proteins through translation and also replicate to form RNA strands, or the viral RNA may make MRNA using their own and host cell enzymes (negative sense RNA virus) and thus make proteins through translation and make RNA strands through replication with the aid of RNA dependent RNA polymerase enzyme. Sometimes viral RNA may be converted to DNA through the aid of reverse transcriptase enzyme. This new DNA copy will integrate with the host DNA and thus transcribe the MRNA to make proteins and copies of viral RNA. No matter which way the RNA and proteins are replicated and translated, they will be assembled into active virus particles in the endothelial reticulum attached to the Golgi bodies of the host cells. Finally, the newly formed virus particles emerge from the host cells through endocytosis, by killing the host cell. The new virus then attacks neighboring cells, thus continuing their destruction of the lung tissue.

In causing the COVID-19 disease, the virus typically invades a particular type of lung cells, thereby causing respiratory distress syndrome and in severe cases, death. The SARS-CoV-2 virus enters the respiratory tract through the nose i.e. nasopharyngeal orifice, or through the mouth or even through eyes or other passages. Whichever way, it makes entry into trachea, bronchi, bronchioles, and finally into the alveoli. The entire human lung structure is like an inverted tree i.e. trachea being trunk, bronchi being two main branches, bronchioles being subbranches of the main two branches, and finally the twig and leaves comparable to alveoli of lung. There are millions of alveoli, which are the crucial parts of the lungs to introducing oxygen and to removing carbon dioxide from the blood.

The conducting pathways of the respiratory system's nasal cavity, trachea, bronchi, and bronchioles are lined by the pseudo stratified columnar epithelial tissue, which is ciliated, and which includes intermittently located mucus secreting goblet cells. Incoming particles such as dust, bacteria, and virus adhere to the mucus, which is then swept away by the cilia. The alveoli are lined by simple squamous epithelium. These are called type-I pneumocytes, which are primarily responsible for gas exchange (oxygen and carbon dioxide). Scattered among these squamous cells are occasional larger cuboidal cells and these are also called type-II pneumocytes. These cells secrete surfactant, which prevent alveolar walls from sticking to one another, to maintain the contour and also efficient functionality of the alveolus.

The COVID-19 virus SARS-CoV-2 preferentially attacks the ciliated cells of the upper respiratory tract and also the type-II pneumocytes in the alveoli, thus causing inflammation and pneumonia.

According to a hypothetical progression of the disease in a human, as soon as the virus enters into the human respiratory tract and starts the infective process, the first line of defense, the lung macrophages, start to attack the virus. In addition, the defensins produced by respiratory tract epithelial cells and also neutrophils to inactivate the virus. If the infected person has previously produced antibodies, these will also inactivate the coronavirus. Consequently, if the above systems operate efficiently, the infection will not even affect the person. A percentage of exposed people, perhaps as high as 80 to 85 percent, can be expected to be asymptomatic although they were exposed to the virus.

According to a further level of hypothetical operation, if someone does not have any antibodies (through lack of previous exposure to COVID-19 or exposure to a similar genome as COVID-19) or proper defensins, the lung macrophages, neutrophils and NK-cells (the innate immunity soldiers) will detect the virus and the virus infected cells and start to inactivate or destroy them. If the COVID-19 viral concentration is high, then cytokines (interleukins) are produced which in turn will call for the T-cell intervention through antigen presenting cells. Depending on the major histocompatibility complex and antigen, the T-cells will be are activated to become effector T-cells and/or killer T-cells. These immune cells will kill the COVID-19 virus and also destroy the COVID-19 infected host cells. Because of this activated immune system involving both innate and adaptive immune agents, the infected patient will display a cough and slight increase in fever, more like normal flu symptoms, and will get over the infection in due course, perhaps in a week or so. This result may be expected in a small percentage of exposed people, perhaps fewer than 15% of the exposed population. Technically these people also will develop antibodies to fight off the COVID-19 virus, through intervention of adaptive immune system's B-cells. These 15% of the population who were infected, but recovered, also must have good concentration of the T-regulatory immune cells and the immune suppressing interleukins to simmer the inflammation, in order to eliminate further complications due to autoimmunity.

According to a final level of hypothetical operation, a still smaller percentage of people, perhaps 5%, may be expected to show severe respiratory distress symptoms including severe pneumonia and extreme difficulty in breathing. Apparently, these sectors of people must have suppressed immune system involving both the innate and adaptive immunity. In these people the COVID-19 virus is attacked by lung macrophages and neutrophils, followed by excess production of cytokines producing a cytokine storm. The immune system operates at a slower rate than in the prior hypotheticals, with agents including effector T-cells and Killer T-cells. This more sluggish action of the immune system allows the virus initially to multiply at a faster pace, causing severe damage to the respiratory system. To counteract this, overactive inflammation provoking interleukins and effector T-cells and NK-cells will arrive at the scene. In addition, an excess number of neutrophils will be poured into the lung tissue, increasing the reactive oxidative species. Simultaneously, since the COVID-19 virus starts destroying ciliated lung cells as well as type-II pneumocytes of the alveoli, the mucus, debris, and fluids oozed out of blood start collecting in the upper and lower respiratory system.

With destruction of type-11 pneumocytes, the alveoli experience a lack of surfactant and will collapse and drown in the fluid. Consequently, the patient cannot breathe properly. To make the situation worse, the adaptive immune system becomes overactive and attacks even normal, healthy lung tissue, creating a honeycomb appearance of lung tissue with holes, which create the appearance of ground glass. In addition, the destroyed cellular debris, excess cytokines, and other opportunistic pathogenic bacteria and viruses now gain entrance into the blood and create a systemic infection, including further severe infection by COVID-19 infection and possibly by other pathogenic bacteria, affecting various body parts including heart, kidneys, intestines, and blood vessels, to induce death of the patient.

The described result constitutes an autoimmune attack and results from a lack or reduced concentration of T-regulatory cells and inflammation suppressing interleukins in the systematic circulation. Out of this small, 5% susceptible population, perhaps 60 percent of them may survive with ventilators, since they may have proper concentration of T-reg cells as well as the immune suppressing interleukins like IL-10. The other roughly 35 percent of the small group may die, because of the overactive immune system (secondary autoimmunity) followed by lack of sufficient concentration of T-reg cells and immune suppressing interleukins in their systematic circulation or body, in addition to the established systemic infection due to septicemia involving both the COVID-19 virus and possibly other pathogenic bacteria.

Now, one can appreciate the pathophysiology of the COVID-19 disease. This virus is not as lethal as SARS or MERS, yet it spreads and infects quickly with high percentage (high morbidity) but kills only limited people (low mortality). Thus, this COVID-19 is highly lethal to the old age or geriatric population because of the immune senescence, i.e. decrease T-cell and NK-cell activity in old age. According to the limitedly available statistics, 80% of the COVID-19 deaths are in the population who are 80 to 90 plus years old, 13% of the COVID-19 deaths are in the population of age groups 70 to 80, whereas 7% of the deaths are in the population age group of 60 to 70. However, all other age groups can also be infected and may die due to underlying comorbid diseases, such as heart and kidney diseases, chronic diabetes, hypertension, and excess obesity, with a compromised or underactive immune system involving both innate and adaptive immunity It would be desirable to increase the available options for preventing and treating disease caused by coronavirus. Specifically, the population would benefit from a selectively self-administered preventative treatment that goes beyond such external mode steps as hand washing and mask wearing. Anyone can experience exposure, and if that person knows or just suspects exposure, currently that person is helpless to improve his prospects for avoiding the resultant disease. There is no effective level of hand washing or mask wearing that wards off coronavirus that has already penetrated the external openings such as airways leading into the respiratory system. Once the virus reaches internal mucus membranes, very little can prevent infection.

It can be appreciated that a coronavirus is an assembly of parts held together by chemical bonds. Often it is regarded as not even being alive in its independent state or perhaps the virus should be regarded as being barely alive. Thus, it can be regarded as error to refer to killing the virus, whereas referring to inactivating the virus seems more exact.

Hand washing can be effective to inactivate the virus while external of the body, provided that soap is used. Mere water is largely inadequate by itself. Water fails because the virus is held together by hydrogen bonds and hydrophilic interactions, and the virus adheres to human skin by similar hydrogen bonds. Water has similar hydrogen bonds and, for this reason, is not reliable to wash away a virus bonded to skin by the same type of bond. With the addition of common soap, the result is different. Soap contains fat-like substances known as amphiphiles, which are similar to lipids in the virus membrane. The bonding with amphiphiles is adequate to break the hydrogen bonds between virus and skin, thus allowing the virus to be washed free of the hands. This process of dissolving bonds and washing away virus is known to require considerable time, and active rubbing is desirable in addition to a long soak. Thus, recommended hand washing is specified to require twenty seconds or more to be effective, even when using soap.

Ethanol also can be effective to wash away virus from skin, as ethanol readily forms hydrogen bonds with virus. However, ethanol needs to be of high concentration, such as 60-80% or more, to rapidly dissolve the virus. Therefore, soapy water and high concentration ethanol can be effective external mode washes for virus, provided they are adequately applied.

Known external mode washes are substantially of no value when the virus has reached a mucus membrane within the respiratory system. It is readily appreciated that human airways and lungs cannot be washed out by scrubbing with soapy water. Likewise, these passages and lungs cannot be washed with high concentration alcohol. Further complicating the situation, the virus in airways and lungs embeds itself in healthy human cells, establishing an embedded mode where it is no longer merely adhered to skin surface, so if removal by washing is even possible, it is a far more difficult task than an external mode surface wash.

Yet, it would be highly desirable to provide a method and means of washing or flushing an internally located virus from mucus membranes, such as found in the mouth, airways, or lungs. Such a method and means would meet the needs of people to self-administer a preventative treatment to ward off a viral disease. This ability would be of immense importance for countless reasons. A few are: (1) providing a break in the chain of virus transmission, especially, but not exclusively, significant in the absence of a vaccine; (2) removing the raw ability to conduct virus treatment of the potentially infected person from the hospital to the home; (3) restoring psychological comfort and courage back to the individual by supplying an effective physical tool answering the virus threat; (4) enabling business of all sorts to reopen at full customer capacity, with individual control ensuring that, at long last, a nearby person need not constitute an unanswerable health threat of hopeless contamination; (5) allow sensible reorientation of government at all levels to function in more than singular crisis mode of dealing with the virus pandemic.

To achieve the foregoing and other object and in accordance with the purpose of the present invention, as embodied and broadly described herein, the method and apparatus of this invention may comprise the following.

BRIEF SUMMARY OF THE INVENTION

Against the described background, it is therefore a general objective of the invention is to inactivate the SARS-CoV-2 coronavirus even after it transitions from an external mode by entering airway or lungs.

An important object is to create a multiphase defense against a coronavirus, in which one phase is a near entry point lysing phase and another phase is an immune system enhancement phase, such that the lysing phase weakens or clears virus that can be reached by an internally applied effective lysing agent, thus reducing the overall internal numbers of the virus to correspondingly reduce the numbers of virus binding with ACE-2 enzyme.

Another object is to inactivate coronavirus regardless of mutation.

A more specific object is to dislodge and inactivate the coronavirus from the nasopharyngeal orifices before the virus is embedded to establish infection.

A more specific object is to dislodge and inactivate the coronavirus from the buccal cavity (oral) before the virus is embedded to establish infection.

Another objective is to inactivate or attenuate the SARS-CoV-2 virus in the lungs' alveolar tissue before the virus is embedded to establish infection.

Another object is to inactivate or attenuate the SARS-CoV-2 virus in the upper respiratory tract and lungs' alveolar tissue by converting the virus as non-lethal antigens to improve host immunity through production of specific antibodies.

A more specific object is to inactivate pathogenic bacteria and DNA and RNA viruses in the nasopharyngeal orifices to eliminate inflammation of the nasopharyngeal epithelium and mucus membranes which is responsible for coronavirus infestation.

Another objective is to inactivate or significantly reduce pathogenic yeast and mold infestation of the nasopharyngeal orifices, which otherwise can further dispose a victim to pick up COVID-19 or other influenza viral infection.

Another objective is to establish probiotics on the nasopharyngeal epithelium as well as in the oral cavity to improve the immune system to ward off the coronavirus, pathogenic bacteria, yeast, and molds.

Another object is to improve the gastrointestinal microbiota, microbiome, and immunomodulation through ingestion of selected probiotics included in a nutritional supplement.

Another object is to improve the production of T-regulatory cells as well as the immune suppressing interleukins by the gut associated lymphatic system, with the aid of multiple strain probiotics and their immunomodulins to reduce cytokine storm and overactive immune system during acute COVID-19 infection, to protect the COVID-19 victim.

Another objective is to increase the bioavailability of ascorbic acid and sodium ascorbate to protect probiotics and thus to prevent or cure the COVID-19 viral infection.

Another objective is to increase the bioavailability of ascorbic acid as a liposome to protect probiotics and thus to prevent or cure the COVID-19 viral infection.

Another objective is to increase the bioavailability as well as the efficiency of ascorbic acid by converting it as sodium ascorbate liposome.

Another objective to enable probiotic bacteria and their immunomodulins to be safely delivered to the distal part of the small intestinal tract by making them as liposomes.

Another object is to make probiotics produced biopeptides and probiotic protecting herbal infusions bioavailable by forming liposomes to deliver them safely into the blood and thus to deliver into the lungs to inactivate or curtail the multiplication of the coronavirus in both the upper respiratory tract and in the alveolus.

Another more specific objective is to develop an effective smelling salt using liposomal probiotics and their volatile growth end products and alcohol dissolved volatile herbal infusions, to activate lung tissue and at the same time inactivate coronavirus through disrupting its lipid envelope.

Another objective is to apply the benefits of cannabidiol (CBD) along with the probiotics and their volatile end products of growth, volatile herbs, to enhance the inactivation of coronavirus and simultaneously decrease the oxidative lung damage due to oxidative reactive species produced by the excessively activated neutrophils during the COVID-19 infection.

Another objective is to apply the combined benefits of CBD and probiotics as an adjuvant to enhance nutritional supplements to boost immune stimulation by the probiotics.

Another objective is to apply the benefits of CBD as an adjunct in a smelling salt to enhance an immune response by the nasal epithelial cells in conjunction with exposure to volatile herbs.

Another objective is to develop a simplified effective smelling salt composition of herbal infusions mixed with alcohol and optionally with CBD to use as a preventive aid to control COVID-19 proximate to time of exposure.

Another objective is to enable inactivation of coronavirus without hospital intervention, to reduce the need for professionals to wear currently recommended, uncomfortable nose masks when attending to patients.

In one aspect, the invention is an effective means and method for controlling the spread of COVID-19 disease. This is achieved by a multi-part, selectively self-administered treatment. In part, the invention is a composition and an administration in the form of a defense that is internally applied to airways to inactivate virus in the airways to whatever extent proves to be possible. Virus inhibiting agents might be a nasal irrigant and an oral gargling mouthwash, which can dislodge and lyse the coronavirus in the nasal pharyngeal orifices as well as in the buccal cavity with positive effect. One goal is to dislodge and inactivate the coronavirus while also improving immunity of the epithelial cells to prevent further infection when practiced properly. In further part, the invention is a novel smelling salt formulated with probiotics-produced volatile immunomodulins and herbal infusions that will lyse the coronavirus by bursting its fat (lipid) envelope. When once the lipid layer of the virus is disrupted prior to the point when the virus is embedded in a human cell, the coronavirus can no longer replicate, which otherwise is a necessary step prior to infecting additional cells. It has been further discovered that the disrupted viral particles may act as antigens in production of antibodies to confer active immunity. Thus, the smelling salt serves two purposes: First, to inactivate and disrupt the COVID-19 virus, and; Second, to help the immune system to produce antibodies using the attenuated or dismantled viral particles.

Another aspect of the invention is to provide a countermeasure to the action of the host immune system in COVID-19 cases to become excessively active, apparently to inactivate the virus. However, this excess activity generates an excess of highly reactive oxidative species in the lung tissue, capable of destroying the lungs. According to the countermeasure, the therapeutic and antioxidant level in the blood is improved and maintained for a sufficient length of time either to prevent or to treat the COVID-19 infection. Thus, the countermeasure provides a sustained massive dose of probiotics-produced immunomodulins, and probiotics protective antioxidants to counteract the excess oxidation produced by the host immune system.

The accompanying drawings, which are incorporated in and form a part of the specification, illustrate preferred embodiments of the present invention, and together with the description, serve to explain the principles of the invention. In the drawings:

DETAILED DESCRIPTION OF THE INVENTION

This invention is primarily to prevent or treat the COVID-19 disease caused by coronavirus SARS-CoV-2, which is highly contagious and spreads from human to human through mere contact. Since the route of infection is through nasal and oral cavities, where the virus ultimately ends up in the lung tissue, the invention is focused on systems to inactivate the virus both in the nasopharyngeal orifices and also in the buccal cavity (mouth until the tip of esophagus).

With reference to the drawings, a nasal irrigation and gargling mouthwash composition was designed to dislodge the viral and other pathogenic microorganisms, using a lysing approach. According to FIG. 1, a starting point for applying a lysing agent such as mouthwash or nasal irrigant is timing, to undertake a treatment at a time when the virus possibly has been encountered but remains in an accessible mucus engagement.

Figure 1:
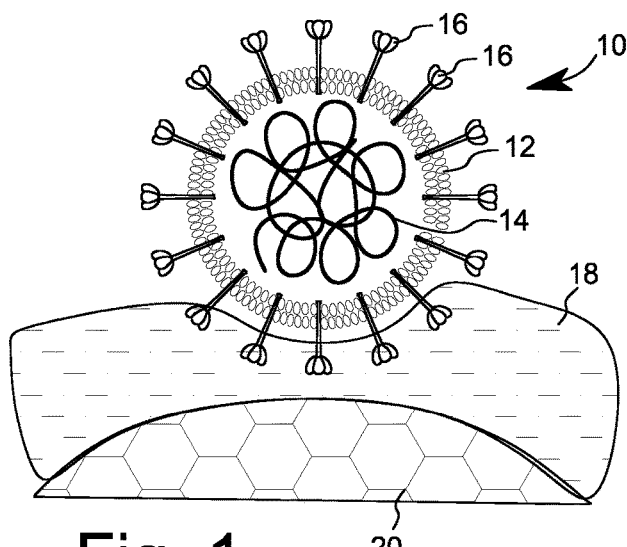
FIG. 1 is a schematic view of a SARS-CoV-2 virus in vertical cross-section, schematically showing a mucus layer and an underlying lung, with the virus lodged in the mucus layer but not the lung tissue.

FIG. 1 shows a schematic virus 10 in cross-section to display an envelope 12 formed of lipids in double layer, bonded together by hydrogen bonds. The envelope contains a strand of RNA 14. The envelope carries a plurality of spike proteins 16 that are useful to seat the virus at a reception site in the human respiratory passages. For best result when an irrigant is being used, the virus might be lodged in a mucus layer but is not yet received into a tissue layer represented as lung tissue 20.

Figure 2:
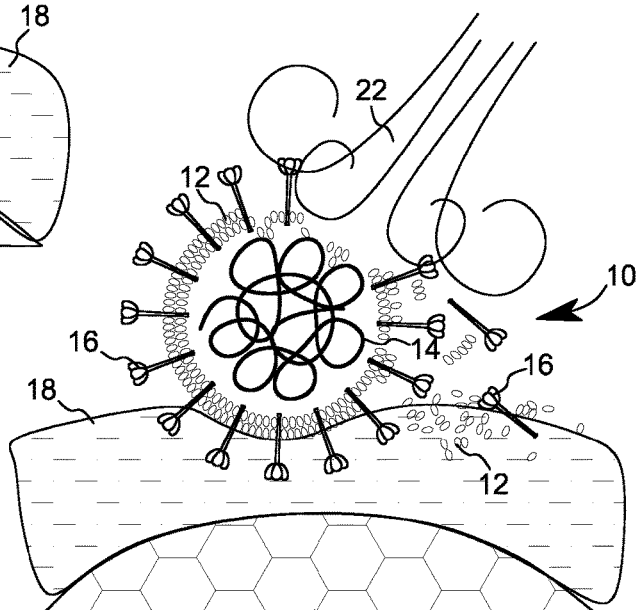
FIG. 2 is a view similar to FIG. 1, showing a progression of the invention in which, a treating composition disrupts the fat layer of the virus and the virus starts to decompose.

Advancing to FIG. 2, an irrigant 22 is applied against the virus, advancing the lysing approach. A suitable irrigant preferably is a liquid. The composition of the liquid includes probiotic immunomodulins and probiotic protecting surfactants and antioxidants which are effective as applied to dissolve or significantly weaken the lipid layer 12 of the envelope. A coronavirus is known to have a fat envelope 12 held together by hydrogen bonds, which characteristically are rather weak. The assembled structure of a coronavirus is helpful in maintaining the virus in assembled form, but damage to the assembled form can lead to a failure of the entire structure. Thus, FIG. 2 suggests that a probiotic produced solubilizing agent along with the probiotic protective surfactants can initiate structural failure by limited engagement with the surface of the envelope.

Figure 3:
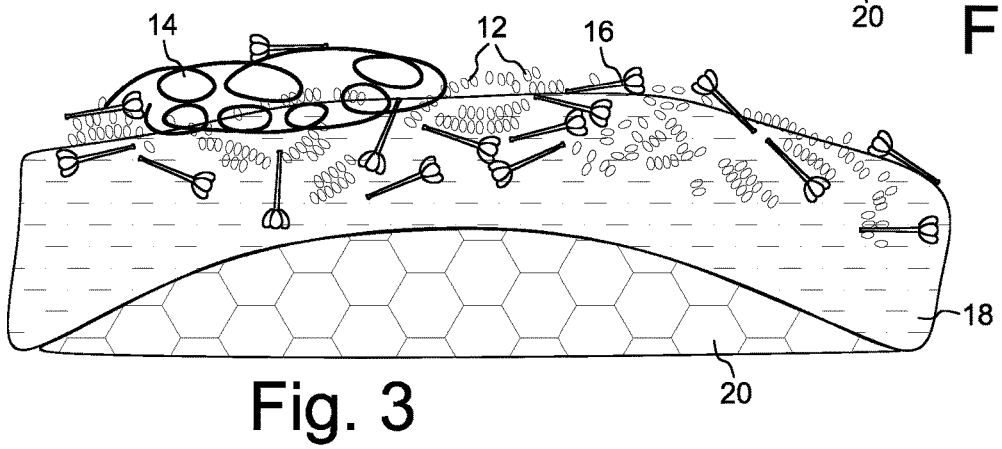
FIG. 3 is a view similar to FIG. 2 in which decomposition of the virus has progressed to inactivate the virus.

Advancing to FIG. 3, the irrigant has completed the lysing approach and initiated structural failure, leading to collapse of the virus structure. The suggestive schematic view of FIG. 3 proposes that the virus may fall apart into any combination of loose components. The RNA strand 14 has come out of the lipid envelope 12 and now is inactive to perform its viral duty of reprogramming a human cell to reproduce the virus. The lipid envelope has fallen apart after the initial failure where it encountered the cloud of solubilizing agent and surfactants 22. Likewise, the spike proteins 16 have fallen from the lipid envelope and are scattered. It will be understood that the drawings present only a visual aid that is hypothetical and simplified in showing an arrangement of the virus and its collapse. However, the drawings make the point that a damaged or collapsed virus located outside a receptor site is inactivated and no longer is capable of replicating itself. It is further postulated that the loose components of FIG. 3 may serve as a source to aid the human immune system in fabricating a vaccine-like response to a future encounter with the virus.

To achieve the destruction of the virus in the airways, upper respiratory tract, and in the alveoli, a smelling salt base is prepared. The salt fractions (base) were sterilized using mild sodium hypochlorite solution. After sterilization, the organic herb extracts as distillates and alcohol infused herbs were added to inactivate the sodium hypochlorite and also to imbibe them onto the sterilized salt mixture. It has been found that such hypochlorite sterilized smelling salt bases (magnesium sulfate plus sea salt) absorbed and maintained the volatile fractions of the complementary probiotics plus their volatile immunomodulins plus probiotic protecting and activating herbs for a longer period with greater efficacy. Apparently, an unexplained biochemical reaction must have happened which facilitated this exceptional character of the salt mix to hold the volatiles intact and improve their shelf life and efficiency over a long period of time with greater efficacy. Also, the volatiles are released very gradually with inhalation. It was also discovered that a quantity of liquid chloroform can be used to sterilize the salt mix, in the place of sodium hypochlorite, where chloroform is legal to use. In addition, optionally CBD (cannabidiol) was included along with the probiotics and herbs, since it is a powerful antioxidant, which can counteract the reactive oxygen species (oxidants) in the lungs in conjunction with probiotics-produced volatile immunomodulins and virus inactivating nano compounds.

In cases where the inhibition approach may be timed too late to catch a virus before it reaches a receptor, an additional treatment phase may be applied to the prospective patient. In severe cases, the coronavirus SARS-CoV-2 may infect the systemic blood circulation system to cause thrombosis, which has been identified as one of the secondary causes of death due to COVID-19 disease. Angiotensin Converting Enzyme-2 (ACE-2) is an enzyme attached to the cell membranes of cells in the lungs, arteries, heart, kidney, and intestines. ACE-2 lowers blood pressure by catalyzing the hydrolysis of Angiotensin-II, which is a vasoconstrictor peptide with inflammation provoking properties, into Angiotensin 1-7, which is a vasodilator with inflammation reducing properties. ACE-2 counteracts the activity of the related but different Angiotensin-Converting Enzyme (ACE), by reducing the production and amount of Angiotensin-II (AT-II) and simultaneously increasing the concentration of Angiotensin 1-7 (AT 1-7), thus reducing cardiovascular diseases through reduction of vasoconstriction, inflammation, and resulting thrombosis due to blood clots.

ACE-2 also serves as the entry point into cells for some coronaviruses including SARS-CoV-2 viral particles, which enter lung tissues and start multiplying, in severe cases. A resulting high number of virus particles make entry into the systemic circulation of the blood. The endothelial cells of the blood vessels have ACE-2 on their surface. The SARS-Cov-2 virus attaches to these ACE-2 enzymes and thus renders their functionality ineffective. With ineffective ACE-2, the level of AT-II increases with a significant reduction of AT 1-7. This results in uncontrolled activation of NADPH oxidase enzyme with resultant excess production of superoxide. This superoxide destroys or oxidizes the endothelial cells of the blood vessels, thus disturbing the endothelial homeostasis.

This oxidative damage further proceeds to damage subendothelial layers of the blood vessels with resultant releases and increase of Van Willebrand Factor (VWF) and Clotting Factor-8 into the blood. VWF is a pro blood clotting protein. Factor-8 is a blood coagulant. The VWF binds to Clotting Factor-8 in blood, thus causing the formation of blood clots and inducing severe thrombosis. This is the pathophysiology behind COVID-19 disease to cause blood clots and thus cause death, in addition to the severe damage in the lungs due to overactive immune system and physical tissue damage due to virus. Thus, ACE-2 has a role in enhancing the attachment and proliferation of SARS-CoV-2, causing lung damage and thrombosis. The same mechanism may be taking place in the tissues, where there is an abundant amount of ACE-2 in the human body, such as kidneys, heart, and GI tract. The ultimate tissue damage is due to excess oxidation of the affected tissues due to superoxidative species causing oxidative stress. The reason for more deaths of certain individuals due to COVID-19 virus infection is because of the preexisting comorbid diseases. These might include cardiac, lung, and kidney diseases, diabetes, obesity, and chronic hypertension with excessive existing oxidative stress. The result may be a hypoactive immune system and other deficiencies disrupting the ability to maintain healthy epithelial homeostasis. The peptides produced by growing multiple strain probiotics in proper milk based medium along with bio-available milk calcium significantly decreases the production of Angiotensin-II, which is responsible for vasoconstriction and inflammation in the blood vessels. Thus, even though the ACE-2 is rendered ineffective in advanced COVID-19 disease, the bio-active peptides from multiple strain probiotics can reverse the ill effects of COVID-19 disease i.e. thrombosis.

Within the design of the present therapeutic agents, a therapeutic liposomal oral preparation utilizes relatively long retention viable probiotics and multiple strain probiotic growth end products, nano inhibitory compounds, and therapeutic peptides in addition to the probiotic protective antioxidants employed in the liposomal oral preparation formula. Apparently, the additional antioxidants used in the formula (originally intended to protect the probiotics) in conjunction with probiotic peptides might reduce the harmful symptoms of COVID-19 diseases, to protect the patient. In addition, the antioxidants from the formula will also counteract oxidative stress and inactivate the virus, thus reducing thrombosis and similar negative factors in the blood. The addition of multiple mixed strain probiotics activates the lymphatic system to produce inflammation reducing interleukins and also activates T-reg cells, which will simmer an overactive immune system as encountered in a COVID-19 infection. It may not be presently possible to fully explain the working of orally administered compositions within the invention at molecular level. However, these compositions appear to function well to counteract COVID-19 infection. It is speculated that the combination of bio-active peptides and immunomodulins of multiple strain probiotics along with antioxidants used primarily to protect probiotics, such as ascorbic acid, sodium bicarbonate, sodium ascorbate, synergistically act to reduce or cure COVID-19 infection.

The combination of therapeutic ingredients present in the liposomal preparations of this invention may alter the infection pattern of the COVID-19 disease, perhaps by preventing the attachment of the virus to the ACE-2 receptors and at the same time inhibiting the formation of Angiotensin-II, which causes inflammation of blood vessels. Conversely it may also be due to direct inhibition of the SARS-CoV-2 virus by the active principles of probiotics, in conjunction with stabilized liposome antioxidants (which are primarily used to protect the probiotics).

The acute COVID-19 infection significantly increases the inflammation provoking interleukins (cytokines) and excess neutrophils with the production of oxidation inducing molecules, which cause severe damage to lung tissue. To control the above oxidative damage to the lung tissue during the COVID-19 infection, a liposome of multiple strain probiotics, along with their peptides and ascorbic acid, sodium bicarbonate, and sodium ascorbate herbal infusion with CBD was prepared and administered through oral route. Such a preparation significantly improved the recovery of patients from the COVID-19 infection. The liposomal preparation greatly improved the retention of probiotic peptides, ascorbic acid, sodium ascorbate, and active principles of herbs in the blood to reduce oxidative lung damage. It was also discovered that in acute cases of COVID-19, CBD significantly improved the recovery by synergistically accelerating the therapeutic properties of the probiotic peptides, probiotics-protective herbal infusions, as well as the ascorbic acid, sodium bicarbonate and sodium ascorbate present in the liposome.

In this invention, a nasal irrigation composition is prepared using sodium chloride, ascorbic acid, sodium bicarbonate, sodium ascorbate, multiple mixed strain probiotics composed of beneficial strains belonging to genus *Lactobacillus, Bifidobacterium, Streptococcus, Lactococcus, Leuconostoc, Propionibacterium, Brevibacterium, Saccharomyces* and mixtures thereof, along with their immunomodulins.

The probiotic strains with their immunomodulins are either spray dried or freeze dried, along with mild surfactants and yeast and mold inhibitors (natamycin and sodium propionate), and then mixed with other aforementioned ingredients in an attempt to reduce the nasal irritation. Two and a half (2.5) grams of this dry blended mixture is added to 260 ml of lukewarm water and irrigated the nose using any standard nasal irrigation devices to clear the nasal passages, to dislodge and inactivate the coronavirus, and also to wash out unwanted yeast, molds, toxins, and pathogenic bacteria. It is also intended to implant the beneficial all natural probiotic bacteria on the nasal epithelial cells, to further inhibit the adhesion and multiplication of the SARS-CoV-2 virus as well as all other types of viruses, which can cause viral infections and allergies. The probiotics included in the current nasal irrigation composition are intended to induce optimal immunomodulatory effect through production of T-reg cells, inflammation suppressing interleukins and defensins, which can offset the excess infection and excess inflammation to protect the COVID-19 infected patient.

A similar composition prepared as a liquid was used as mouthwash with gargling to dislodge and inactivate any coronavirus sticking to the oral epithelial cells and the cells up to the epiglottis. Thus, the sputum is free from the corona viral load, to eliminate the spread of infection to others.

This invention is unique in that it can be used individually as nasal irrigation, mouthwash with gargling, smelling salt to inactivate or subdue the virus in the upper respiratory tract and the alveoli, and a liposomal nutritional supplement to improve recovery from COVID-19 infection, as well as a viral preventative aid. All of the above can also be used in various combinations or all together to improve or prevent the COVID-19 infection and other pathogenic viral, bacterial, yeast and mold infections.

The following multiple mixed strain probiotics, multiple herbal infusions, and CBD are included in this invention.

Probiotics—Probiotics are beneficial micro-organisms which when ingested improve the health of the human beings significantly. They are part of the human microbiota and microbiome involving both the gastrointestinal tract as well as the oral and nasopharyngeal orifices. The following is the official definition of probiotics according to FAO/WHO. The probiotics are any live microorganisms which when administered in adequate amounts confer a health benefit on host. It encompasses all applications of live micro-organisms, not just for the gastrointestinal tract. The following multiple mixed strain probiotics are included in this invention: *Lactobacillus plantarum; Lactobacillus rhamnosus; L. paracasei; L. casei; Bifidobacterium longum; Bifidobacterium bifidus; Streptococcus thermophilus; Lactobacillus bulgaricus; Lactococcus lactis* subsp. *lactis; Lactococcus lactis* subsp. *cremoris; Lactococcus lactis* subsp. *lactis* var *diacetylactis; Streptococcus faecium; Pediococcus acidlactici; Propionibacterium shermanii; Propionibacterium arabinosum; Leuconostoc mesenteroides* ssp *cremoris*. All of the above probiotic strains are food grade and are nonpathogenic and nonpyrogenic. They are categorized as GRAS (Generally Regarded as Safe) by Food and Drug Administration's Code of Federal Regulations. In addition, the following probiotic cultures were included only in the nutritional liposomal composition (outlined in this invention) along with other above specific probiotics, to be administered by the mouth: *Brevibacterium linens; Penicillium roquefortii; Penicillium camembertii;* and *Saccharomyces boulardi* etc. Even if some of these probiotics are injured or heat inactivated during the course of the preparation, they can still induce immunomodulation due to their cell wall components and prior growth products. These are termed para probiotics.

The acid producing strains of probiotics were grown in food grade reconstituted media with no allergenic compounds. The beneficial probiotic bacterial population and their therapeutic by-products of growth, such as therapeutic bio-active peptides and nano peptides and other immuno-modulins has been increased to the maximum by using the external pH control system. With some cultures, internally buffered media is used to grow the cultures to obtain the maximum population and their therapeutic by-products. *Propionibacterium* cultures were grown without any neutralization. The above cultures after growth are either freeze dried, spray dried, dried using inert ingredients, or frozen. The penicillium cultures were grown on bread and then pulverized. Some freeze-dried strains were also purchased from a commercial source, which have the least or no end products of growth to be used as control, while studying the importance of the probiotics and their growth end products to curtail COVID-19 infections.

The following are some of the beneficial therapeutic properties of the food grade probiotic microorganisms employed in this invention. The therapeutic probiotics with identified bacteriocins were selected to include in various compositions.

*Lactobacillus plantarum*: it is a lactic acid producing probiotic bacteria. It has the following therapeutic properties: anticarcinogenic, anti-inflammatory, anti-diabetic, anti-obesity, reduces seasonal allergies and irritable bowel syndrome, significantly improves the function of immune system, reduces high blood pressure, reduces anxiety through production of anxiety and stress suppressing neurotransmitters, anti-viral effect on HINI virus and also on coronavirus. It is a novel probiotic candidate as anti-influenza prevention and infection and it has an excellent ability to stick to the epithelial cells.

*Lactobacillus rhamnosus*: it is an excellent naturally occurring probiotic with the following therapeutic properties: prevention and treatment of gastrointestinal infections and diarrhea, stimulates the immune response, excellent adjuvant to enhance immune response following vaccination, reduces several viral infections through its anti-viral activity by shifting the T-helper cells to TH-I, has an excellent ability to stick to the epithelial cells thus exhibiting the wide spectrum inhibitory properties on both pathogenic bacteria and virus.

*Lactobacillus paracasei*: it has significant therapeutic effect due to its immunomodulatory effect to suppress the inflammatory bowel diseases. In addition, even the heat killed bacterial cells of *Lactobacillus paracesei* have significant therapeutic effect, thus it also serves as a para probiotic to stimulate the immune system. This probiotic has high adhesion capacity to stick to the epithelial cells.

*Lactobacillus casei*: the following are the therapeutic benefits of *L. casei*: Stimulates immune system, inhibits viral infections, decreases the incidence colds and influenza, reduces lower respiratory tract infections, inhibits pneumonia, stimulates the immune system among the elderly population, decrease roto virus infection, inhibits respiratory tract infections, inhibits pneumonia due to bacterial infections such as *Pseudomonas aeruginosa*, and inhibits systemic inflammatory response syndrome.

*Bifidobacterium bifidum*: it has the following therapeutic benefits: reduces *H. pylori* infection, irritable bowel syndrome, lung infections, constipation, ulcerative colitis, and necrotizing enterocolitis.

*Bifidobacterium lungum*: it has the following therapeutic functions: helps to reduce infections through stimulation of immune system, and reduces production of chemicals that increase inflammation and oxidative stress.

*Streptococcus thermophilus*: it has the following proven therapeutic benefits: it significantly improves skin health through hydration when applied as a cream; reduces lactose intolerance, mucositis, gastritis, ulcerative colitis and antibiotic associated diarrhea; it exerts anti-inflammatory effect by suppressing TH-I, it stimulates macrophages, T-cell regeneration, and immunological defense mechanism in human stomach cells.

*Lactobacillus bulgaricus*: it has the following therapeutic effects: decreases common colds due to viral infections, allergic rhinitis, periodontal diseases and other oral health problems; decreases eczema, leaky gut, inflammation, triglycerides—LDL—and total cholesterol; significantly improves immunity, and fights viruses, and improves longevity.

*Lactobacillus sporogenes*: also called *Bacillus coagulans*. It has the following therapeutic effects: it improves immune system and significantly decreases respiratory infections: acts as an adjuvant to improve vaccine efficiency; decreases roto viral diarrhea, traveler's diarrhea, diarrhea caused by antibiotics, *Helicobacter pylori*, irritable bowel syndrome (IBS), and inflammatory bowel disease (IBD).

*Lactobacillus acidophilus*: it has the following therapeutic benefits: decreases depression, chronic fatigue syndrome, sleep problems, muscle or joint pain, extreme tiredness, lactose intolerance, irritable bowel syndrome; decreases cholesterol, over growth of *candida* which is responsible for itching and painful skin, and significantly boost the immune system.

*Lactococcus lactis* subsp. *lactis*: it has the following therapeutic benefits: improves the skin health, activates the plasmacytoid dendritic cells which improve both the innate and adaptive immune responses, activates the natural killer cells (NK cells) and enhances their cytotoxic activity, improves resistance against pneumococcal infections, and reduces lung damage due to influenza virus and HINI infection. Even the para probiotic fractions of this bacterium reduce allergic response, reduce bronchitis and alveolar inflammation, reduce blood pressure, LDL cholesterol, and triglycerides, reduce age related hearing loss, and induce cancer cell death.

*Lactococcus lactis* subsp. *cremoris*: it has the following therapeutic properties: antioxidant, improves overall gut health, antidepressant, decreases anxiety, exhibits significant inhibitory effect on *Listeria monocytogenes*, up regulates anti-oxidation metabolites such as folate and glutathione, also down regulates the enzymes producing ROS (thus reducing oxidative stress) and has a significant effect on free radical scavenging to reduce oxidation of the tissues.

*Lactococcus lactis* subsp. *lactis* var *diacetylactis*: it has the following knew known therapeutic properties: antifungal and antimicrobial.

*Streptococcus faecium*; it has the following therapeutic properties: produces a broad spectrum of bacteriocins to prevent infections due to *H. pylori, C. difficile, L. monocytogens* and *Salmonella*; exhibits the immunomodulation property along with enhanced production of cytokines and T-reg cells, has anti-inflammatory effect through production of butyrate to improve intestinal epithelial cell integrity. The *S. faecium* food strains are safe and significantly improve gut health.

*Pediococcus acidolactici*: it has the following therapeutic effects: reduces constipation, diarrhea, stress; significantly improves immune response; suppresses auto immune encephalomyelitis by inducing IL-10 producing regulatory T-cells.

*Leuconostoc mesenteroids* subsp. *cremoris*: the following are their therapeutic properties: strong antimicrobial property to inhibit several pathogenic bacteria in the gastrointestinal tract, exhibits similar therapeutic properties as *Lactobacillus plantarum* in terms of adhesion, antimicrobial properties, and anti-inflammatory properties.

*Propionibacterium shermanii* and *Propionibacterium arabinosum*: they have the following therapeutic properties: regulate intestinal microflora to arrive at the optimal concentration of microbiota and microbiome, produce bacteriocins to inhibit the pathogenic bacteria, have an exceptional ability to scavenge mycotoxins to minimize mutagenesis of the epithelial cells, stimulate *Bifidobacterium* which in turn create homeostasis among other beneficial bacteria, and antifungal by producing propionic acid.

*Brevibacterium* linens: the following are the therapeutic properties: excellent immune stimulator, reduces tumor incidence, improves digestion, reduces serum cholesterol, is highly proteolytic and lipolytic and thus can inactivate coronaviruses having lipid protective layer.

*Penicillium roquefortii* and *Penicillium camembertii*: these are food grade molds. The metabolites of food grade-*P. roquefortii* (andrastins A, B, C, and D) are potential inhibitors of cholesterol biosynthesis and thus contribute to cholesterol reduction; andrastin-A has strong antitumor properties; the metabolite roquefortine inhibits gram positive pathogenic bacteria, has anti-inflammatory and proregenerative properties; and food grade *Penicillium camembertii* also produces fat breaking and protein breaking enzymes and thus serves as a good digestive aid to curtail digestive disorders.

*Saccharomyces boulardi*: a food grade yeast that prevents and treats intestinal diseases, has immunomodulatory effect, significantly improves the bio-availability of minerals, detoxifies mycotoxins and thus protects the epithelial cells, lowers serum cholesterol, is an anti-oxidant and anti-mutagenic, and also has significant anti-tumor and anti-inflammatory properties, and reduces the risk of cardiovascular diseases, cancer, and Alzheimer's diseases.

The following herbs with the listed therapeutic properties were evaluated to be infused into alcohol, to be used selectively in the inhaling salt and the liposomal composition for oral administration:

1. *Accacia murrayana* (botanical name), the common name is Acacia. It has the following therapeutic properties: reduction of cholesterol, blood sugar, obesity, and IBS (irritable bowel syndrome).

2. *Aloe barbandensis* miller (botanical name), the common name is Aloe. It has the following therapeutic properties: antioxidant, antibacterial, and healing aid.

3. *Swertia chirata* (botanical name), the common name is Chirata. It has the following therapeutic properties: reduces hypoglycemia, fever, malarial fever, dyspepsia, and diarrhea.

4. *Anethum graveolens* (botanical name), the common name is Dill. It has the following therapeutic properties: antiviral, antifungal, anti-inflammatory function, antibacterial, antioxidant, and helps cell division and DNA replication.

5. *Cynara scolymus* (botanical name), the common name is Artichoke. It has the following therapeutic properties: reduction of asthma, eczema, fever, obesity, cholesterol, and liver disorders.

6. *Inula helenium* (botanical name), the common name is Elecanpane. It has the following therapeutic properties: strengthens the integrity of mucus tissue of the respiratory tract, helps mucus secretion through stimulation of respiratory tract mucus cells in trachea, and helps respiration.

7. *Gentian rhizome* (botanical name), the common name is Gentian or Bitter Root. It has the following therapeutic properties: improves the overall health of the sinuses, supports digestion and gut health, and helps to reduce hypertension.

8. *Paulinia cupana* (botanical name), the common name is Guarana. It has the following therapeutic properties: reduces mental and physical fatigue, and significantly improves athletic performance and overall stamina.

9. *Krameria triandra* (botanical name), the common name is Phatany Root. It has the following therapeutic properties: reduces enteritis, chest pain (angina), and mouth and throat irritation.

10. *Aristolochia serpentaria* (botanical name), the common name is Serpentaria. It has the following therapeutic properties: reduces fever, sore throat, inflammation and viral infections; improves the blood circulation and also acts as a nervous stimulant.

11. *Valeriana officinalis* (botanical name), the common name is Valerian. It has the following therapeutic properties: treats insomnia, anxiety, and headache, and relieves stress.

12. *Veronica spicata* (botanical name), the common name is *Veronica*. It has the following therapeutic properties: antioxidant, diuretic, expectorant, improves overall lung function, heals sore throat and liver problems.

13. *Curcuma longa* (botanical name), the common name is turmeric. It has the following therapeutic properties: antioxidant, anti-inflammatory agent, antiaging, stimulates body's own antioxidant systems such as glutathione, andalpha lipoic acid, effective free radical neutralizer of the end products of electron transport systems in the mitochondria, improves heart health, reduces depression, reduces cancer (reduction of angiogenesis), and assists Alzheimer's disease treatments.

14. *Apis millifera* (botanical name), the common name is Honey. It has the following therapeutic properties: antioxidant, antiseptic, anti-inflammatory agent, helps faster wound healing, also reduces cholesterol, blood pressure, cough, allergies, and allergic rhinitis.

15. *Cinchona officianalis* (botanical name), the common name is *Cinchona*. It has the following therapeutic properties: used to treat malaria successfully due to its alkaloid quinine, reduces fever, excellent antimicrobial, and antiviral agent.

16. *Prunus avium* (botanical name), the common name is Wild Cherry. It has the following therapeutic properties: antioxidant, antimicrobial, anti-inflammatory agent, antidiabetic, reduces neurodegeneration and oxidative stress due to free radicals.

17. *Lavrus nobilis* (botanical name), the common name is Bay Leaf. It has the following therapeutic properties: antioxidant, antiseptic, digestive enzyme(s) stimulant, and has properties to reduce cancer (anti-cancer).

18. *Rubus fruticosus* (botanical name), the common name is Black Berry. It has the following therapeutic properties: antioxidant, antimicrobial, anti-cancer, anti-dysentery, antidiabetic, and anti-diarrheal.

19. *Bryonia dioica* and *Bryonia alba* (botanical names), the common name is *Bryonia* Root. It has the following therapeutic properties: reduces chronic inflammation and chronic constipation, antipyretic, cough suppressant, expectorant, reduces pneumonia, bronchitis, and various pulmonary disorders, and reduces pericarditis.

20. *Ocimum basilicum* and *Ocimum sanctum* (botanical names), the common names are Basil and Holy Basil. They have accordingly the following therapeutic properties: antioxidant, antimicrobial, anti-inflammatory agent; improves health of the gut, is a digestive-aid, and improves skin texture and health.

21. *Medicago sativa* (botanical name), the common name is Alfalfa. It has the following therapeutic properties: reduces asthma, arthritis, cholesterol, and blood sugar, is both an antioxidant and an anti-inflammatory agent.

22. *Jateorhiza palmata* (botanical name), the common name is Calumba Root. It has the following therapeutic properties: improves the digestive tract health and digestion.

23. *Syzygium aromaticum* and *Eugenia caryophyllata* (botanical name), the common name is clove. It has the following therapeutic properties: reduces oral and nasopharyngeal inflammation by serving as analgesic, and reduces cough and inflammation of the alveoli.

24. *Coriandrum sativum* (botanical name), the common name is Coriander. It has the following therapeutic properties: antioxidant, anti-diabetic, anti-bacterial, excellent immune booster, digestive-aid, and improves heart and brain health.

25. *Zingiber officinale* (botanical name), the common name is Ginger. It has the following therapeutic properties: antioxidant, anti-inflammation agent; reduces blood sugar, cholesterol, certain cancers, and respiratory infections; is anti-viral, and anti-bacterial, and reduces chronic indigestion, muscle, and joint pain.

26. *Cinnamonum verum* (botanical name), the common name is Cinnamon. It has the following therapeutic properties: antioxidant, anti-inflammation agent, improves insulin sensitivity of the cell receptors, anti-diabetic, and reduces heart diseases.

27. *Cuminum cyminum* (botanical name), the common name is Cumin. It has the following therapeutic properties: antioxidant, anti-microbial, anti-fungal, anti-diabetic, and promotes weight loss.

28. *Piper nigrum* (botanical name), the common name is Black Pepper. It has the following therapeutic properties: antioxidant, anti-inflammation agent, anti-viral, controls blood sugar and cholesterol, reduces common cold and cough, and reduces cancer.

29. *Vanilla planifolia* (botanical name), the common name is Vanilla. It has the following therapeutic properties: antioxidant, anti-bacterial, aphrodisiac-stimulates sex hormones, reduces cough, cold and various pulmonary infections, and reduces gut inflammation and body weight.

Herbal extracts can be made from natural sources or purchased from commercial sources.

A currently available commercial source of therapeutic herbal infusions is any of several blends of spirits and botanicals produced by Natural Spirits USA LLC of North Charleston, S.C. The product line is known to include 90 proof Bio-Whiskey and 80 proof Bio Delight rum, each infused with sixteen botanicals, and 80 proof Bio Club vodka infused with aloe, honey, and vanilla. The therapeutic effect of the rum was tested by therapeutic consumption to alleviate the viral, bacterial, yeast and mold infections causing chronic sneezing, occasional fever, excess uncontrollable mucus production, and lack of sleep. Specifically, the rum was tested for over one year on a patient with chronic cough plus the above specified symptoms, with good results. The testing was done prior to arrival of the COVID-19 pandemic. Apparently, the infection was due to different viral genome than the COVID-19, SARS-CoV-2. The likely cause was a pathogenic bacteria, yeast, and mold infection in combination with an unidentified coronavirus or variant of human influenza virus.

The patient was asked to consume one ounce a day of the rum under evaluation without diluting it with water. The patient was asked to swirl it in the mouth and then consume the rum through sipping.

The following results were obtained: the patient gradually got over the chronic cough and excess mucus production. According to the patient, the results started showing after two weeks and the symptoms totally disappeared in two months. Yet the patient continued consuming an ounce of rum infused with therapeutic herbs for two more additional months for the best results. In this particular case no other allopathic treatment was of any help to cure the chronic continuous cough with excess uncontrollable mucus secretion.

The logical explanation to this phenomenon is that the herbs infused in alcohol exhibited an anti-viral effect apparently through absorption into blood and thus emitting through the pulmonary system. An evaluation based on mere smelling of botanicals-infused rum showed little or no effect on reducing the chronic cough, indicating that oral consumption, without any dilution, was the preferred administration technique. In another patient, similar results were obtained with consuming the botanical-infused whiskey. The botanical-infused vodka also was tested without a control study, and according to some of the cough victims, the infused vodka also produced a therapeutic effect.

Of the three commercial spirit choices, the best anti-viral and anti-microbial results were observed with the botanicals-infused rum, followed by botanicals-infused whiskey and then the botanicals-infused vodka.

A next step was to develop a nasal inhaling therapeutic agent. Although the reported evaluations were not run on patients with COVID-19 disease, it was elected to use the botanicals-infused Bio Delight brand rum as a base to further infuse other selected highly concentrated herbs such as holy basil, clove, turmeric extract, and optionally CBD into a smelling salt targeting the prevention or cure of a coronavirus infection, specifically COVID-19 disease, along with the liposomal multiple strain probiotics with their volatile growth end products and immunomodulins. The commercial botanicals-infused rum was chosen only as a base that now was further enhanced to form the therapeutic agent. Additions to the base were of selected, concentrated, alcohol-extracted herbal extracts, and concentrated herbal distillates. The enhanced product is for use in inhalers to treat coronavirus infections in the respiratory system. The formulation of the enhanced product is not limited by a need to maintain a beverage quality but was open to such development as needed to provide therapeutic effect through nasal inhalation.

The above specified herbs included in Bio-Delight rum and Bio-whiskey were tested against the probiotic strains selected, using disk assay, after alcohol is evaporated leaving the residual herbs on sterile paper disk. It significantly proved that the concentration of herbal extracts in Bio-Delight Rum and Bio-whiskey are not inhibitory to the probiotic strains tested. Even after infusing the Bio-rum (with already infused multiple herb extracts) with additional herbal extracts of basil, clove, and turmeric, the test proved that the selected probiotics included in our formulas were not inhibited. Furthermore, basil, clove, and turmeric herbal extracts exhibited stimulatory effect on probiotic strains, indicating that the herbal extracts, at a concentration used in the current invention, protected and prolonged the viability of the probiotics, which is of a great significance.

As an alternative to establish a scope of suitable base materials, commercial grain alcohol, 95% pure, was evaluated as a base material. Multiple herbs were infused into grain alcohol, producing a similar nasal inhalant. This test showed that the starting base is not limited to a particular commercial infusion of botanicals. It can be formulated from individual ingredients as well as pre-made infusions as a base. However, premade alcohol infusions such as the commercial infused rum or infused whiskey provide a convenient starting material containing at least a small sampling of botanicals.

To administer some of the products of the invention, the following procedure was developed to prepare a liposome of multiple strain probiotics along with their growth end products, such as bacteriocins, immunomodulins and bio-active therapeutic peptides, and other supporting antioxidants which will not only protect but also can enhance probiotic effects in the formulation, which includes ascorbic acid, sodium bicarbonate, sodium ascorbate, plus herbal extracts, and CBD.

Powdered ascorbic acid (20 grams) was weighed and placed in a sterilized beaker, and roughly 100 ml of distilled water is added. The mixture was stirred to dissolve the ascorbic acid in the water. Then gradually with stirring, 7.5 grams of sodium bicarbonate was added to convert part of the ascorbic acid to sodium ascorbate. These reactions generate lot of bubbles. The resultant mixture was a combination of ascorbic acid and sodium ascorbate, which has buffering property. An additional amount of sodium ascorbate is added to this mixture.

Lecithin granules or liquid (30 grams) was weighed and added to 200 ml of water and blended to uniformly to mix the lecithin in an aqueous phase. To this liquefied lecithin, 100 ml of the ascorbic acid, sodium bicarbonate, and sodium ascorbate solution and the liquid or powdered multiple mixed strain probiotics along with their growth end products, bio-peptides and immunomodulins were added and blended for 1 to 2 minutes. At this stage, the herbal extracts and CBD solution or powder was incorporated into the mix and it was blended for an additional 2 minutes. The mix was then sonicated, preferably for about 8 to 16 minutes or longer. The mix can be stored in the refrigerator for 1 week to 2 weeks or can be frozen or can be dried as powder using an inert base such as cellulose or maltodextrin or it can be freeze dried or spray dried. These dried preparations can be tableted or capsulated for convenience of storage, prescribed dosage, or for convenience of transportation.

Cannabidiol (CBD) is a naturally occurring compound found in the resinous flower of *cannabis*. CBD is a phytocannabinoid with a marvelous therapeutic profile. Although CBD is closely related to another phytocannabinoid, Tetrahydrocannabinol (THC). However, unlike THC, CBD is not a psychoactive compound and does not cause an intoxicated feeling. CBD and THC act in different ways on different receptors in the brain and body. German scientists found that CBD stimulated neurogenesis, which has a great significance in resolving several neurological diseases. In addition, according to the published literature, CBD has therapeutic properties or has a significant potential as a treatment aid for a wide range of diseases or maladies. Some of them are: neuropsychiatric illness (autism) and alcoholism; gut disorders such as colitis and crohn's; skin diseases such as dermatitis, acne, and psoriasis; metabolic syndromes such as diabetes and obesity; autoimmune diseases involving excess inflammation such as rheumatoid arthritis and immune disorders; neurological conditions such as Alzheimer's, dementia, Parkinson's disease, multiple sclerosis, stroke, and traumatic brain injury.

CBD has been proven to be neuroprotective, and it has significant effect as an anticancer therapeutic compound.

CBD is effective through the endocannabinoid system to curtail several maladies. Human beings have a built-in endocannabinoid system (ECS) in their physiological constitution. The ECS is represented by two major receptors. They are CB-1 and CB-2. The CB-1 receptors are primarily found in the brain and the central nervous system, and to a lesser extent they present in other body tissues. The CB-2 receptors are mainly located in peripheral organs, especially with the cells associated with the immune system. The human ECS plays an important role in regulating the following physiological vital functions: immune system regulations; blood glucose maintenance to control or eliminate type-II diabetes; maintenance of optimum blood pressure; reducing stress, pain, hunger, and mood change through hormonal control; maintaining overall energy level in the body; and maintaining gastrointestinal metabolic activities.

Improper functioning of the ECS, whether under active or overactive, subjects the human body to several disease conditions. Limited research is already demonstrating that, if the ECS is deregulated, several pathological conditions emerge in human physiology. Thus, modulating the ECS is an essential requisite as a preventative measure for good health, as well as a clinical measure to stop progression of disease. The Human body naturally produces cannabinoids. These are called endocannabinoids. They act on the human (ECS) to help regulate several physiological functions. The hemp derived CBD encourages the human body to produce more endocannabinoids to improve the ECS to maintain homeostasis.

The United States Drug Enforcement Administration (DEA) maintains classification schedules of drugs. Schedule I classification is reserved for drugs considered to have no medical value. Schedule-V classification is for the least dangerous drugs under the Controlled Substances Act. In September 2018, the DEA removed CBD from Schedule-I and reclassified it to Schedule-V under limited circumstances. The limited conditions include that cannabis-derived CBD products could have Schedule-5 status as long as their THC level is below a specified low level. The status of CBD further changed in December of 2018 when the Agricultural Improvement Act removed CBD from the Controlled Substances Act provided the CBD has less than 0.3% THC. Thus, hemp derived as cannabis no longer is an inherently illegal substance under federal law. It remains subject to the same authorities and requirements as FDA regulated products containing any other substance. This is true regardless of the source of the substance, including whether the substance is derived from a plant that is classified as hemp under the Agriculture Improvement Act.

An aspect of the invention is to improve the efficiency of multiple probiotics and their therapeutic end products of growth and herbal components by suitably blending all the ingredients. In particular, the efficiency of CBD can be improved by incorporating it into a blend with several selected herbs and multiple strain probiotics. The importance of minimizing CBD as an ingredient of a blend follows from reports that large doses of CBD may harm the patient. The value of using only a significantly minimal quantity of CBD is that its therapeutic value still is maintained, even when used in such a small quantity, when present in combination with the other complementary multiple strain probiotics along with their growth end products (with significant therapeutic value) and herbal extracts and other antioxidants, due to synergy.

Generally, the optimal dosage of CBD is about 0.1 gr (100 mg) to 1 gram (1000 mg) per application. According to the invention, the optimal CBD dose in a suitable blend can be cut by 90 to 99 percent and yet have the same efficiency. This improvement follows from the use of liposomes to administer CBD. The percentage of improvement is measured against functionality of straight CBD. Probiotics and their immunomodulins further boost the CBD effect. In turn, CBD in blends also boosted the effect of both probiotics and the herbal extracts, which is viewed as a matter of synergy.

The ability to use smaller doses of CBD is further beneficial because it relieves the historical stigma of using high doses of CBD. The reduced quantity of CBD also is helpful by minimizing any adverse effect on the patient of using too much CBD in a mixture of probiotic and antioxidant herbal extracts. Cannabis oil was (with all cannabinoids including the CBD) was evaluated in the place CBD in the formula, with equally good results.

Testing of cannabis oil, complete with CBD, THC, and other cannabinoid compounds, further showed good effect when administered as a liposome. Consequently, administration as a liposome appears to be a key improvement in using minimized dosages of even synthetic CBD or THC or mixtures of CBD, THC, and other cannabinoids that are naturally present in cannabis. The CBD derived from hemp with less than 0.3 percent THC also performed well with minimized concentration when administered as liposome to control viral infections including COVID-19.

The following examples further illustrate the composition, utility, and method of preparing the products of this novel invention.

Example 1—The following dry composition, when dissolved in water, serves as sinus flush or for nasal irrigation. The composition consists of sodium chloride, sodium bicarbonate, ascorbic acid, sodium ascorbate, multiple mixed strain probiotic cultures, powdered glucose oxidase enzyme, yeast and mold inhibitor(s) and a surfactant. Sodium chloride serves as a saline solution after it is dissolved in water, since it is isotonic. Ascorbic acid is Vit-C powder, which serves to protect the multiple probiotics and their growth end products including bio-active therapeutic peptides, bacteriocins, and immunomodulins and in addition also strengthen the nasopharyngeal epithelial cells. Sodium bicarbonate serves as a surfactant and also reacts with ascorbic acid to form sodium ascorbate, which serves as a buffer to protect probiotics and also a surfactant. Sodium ascorbate is produced by dissolving ascorbic acid in water and adding an equivalent amount of sodium bicarbonate in water, resulting in a reaction with effervescence. By mixing nonequivalent amounts of sodium bicarbonate and ascorbic acid, the reaction will not consume the major component, allowing continued presence in the composition of the major component. The multiple mixed strain probiotics and their immunomodulins improve immunomodulation and also serve as inhibitors of pathogenic viruses and bacteria. A spray dried blend of yeast and mold inhibitors, surfactants, and oxidase enzyme, in the formula, significantly assists the activity of probiotics to inactivate not only the irritation creating yeasts, molds, toxins, pathogenic bacteria, but also pathogenic virus including the influenza virus and coronavirus causing COVID-19. The surfactant, polysorbate, present in the blend not only serves primarily as a nutrient for probiotics but also assists in dissolving the lipid layer of the coronavirus causing COVID-19. The following optimal composition of the sinus flush or nasal irrigation has been arrived at by going through a series of experiments and is presented in Table-1 and Table-2.

TABLE 1

The composition of the nasal probiotics irrigation powder/100 grams

| Ingredient | Quantity (grams) | Typical range (grams) | Preferred range (grams) |
|---|---|---|---|
| Multiple probiotics strain blend (powder)[1] | 4.0 | 0.1 to 5.0 | 0.75 to 4.5 |
| Sodium chloride[4] | 80 | 75 to 95 | 80 to 90 |
| Sodium bicarbonate[2] | 7.5 | 5.5 to 9.0 | 6.5 to 8.0 |
| Ascorbic acid[2] | 4.0 | 2.0 to 6.0 | 3.50 to 4.5 |
| Sodium ascorbate[2] | 1.0 | 0.5 to 2.0 | 0.75 to 1.75 |
| Cannabidiol (oil)[2] | 1.1 | 0.50 to 4.0 | 1.0 to 2.25 |
| Spray dried natamycin + Sodium propionate + Glucose oxidase + Polysorbate 60 + Vit-E (powder)[3] | 2.2 | 1.5 to 5.0 | 1.5 to 3.5 |

[1]Principle active ingredient
[2]Primary probiotic protecting antioxidants
[3]Secondary probiotic stimulants and adjuvants
[4]Isotonic solution ingredient upon dissolving the formula in water

TABLE 2

Proximate composition of each ingredient in 2.5 grams of probiotic irrigation powder and quantity of each ingredient per ml when 2.5 grams powder is dissolved in 260 ml of water presented both in milligrams as well as parts per million (PPM).

| Ingredient | Quantity of each ingredient in 2.5 grams of powder | Quantity of each ingredient when 2.5 grams of powder is dissolved in 260 ml water, presented as concentration of each ingredient/ml | PPM of each ingredient in solution |
|---|---|---|---|
| Multiple strain probiotic strain blend along with their growth end products (powder)[1] | 0.10 g | 0.38 mg | 380 |
| Sodium chloride[4] | 2.0 g | 7.69 mg | 7,690 |
| Sodium bicarbonate[2] | 0.18 g | 0.69 mg | 690 |
| Ascorbic acid[2] | 0.10 g | 0.38 mg | 380 |
| Sodium ascorbate[2] | 25 mg | 0.10 mg | 96 |
| Cannabidiol (oil)[2] | 32.50 mg | 0.125 mg | 125 |
| Natamycin[3] | 2.75 mg | 10.57 micro-grams | 10.57 |
| Sodium propionate[3] | 18.15 mg | 70.0 micro-grams | 70 |
| Glucose oxidase[3] | 0.24 mg | 1.0 micro-grams | 1 |
| Vit-E[3] | 0.12 mg | 0.5 micro-grams | 0.5 |
| Polysorbate 60[3] | 33.83 mg | 0.13 mg | 130 |

[1]Principle active ingredient
[2]Thitnary probiotic protecting antioxidants
[3]Secondary probiotic stimulants and adjuvants
[4]Isotonic solution ingredient upon dissolving the formula in water 2.5 grams of the sinus flush or nasal irrigation powder was dissolved in 260 ml of lukewarm water present in any nasal irrigation device. After it is dissolved, the mixture was used for nasal irrigation administered through alternate nostrils. If the condition is severe, it is practiced on a daily basis. If not, it can be done twice a week or whatever is convenient for preventative purposes.

Results are surprisingly clear in that it totally eliminated the allergies, influenza viral infections, and coronavirus infections including the SARS-CoV-2. In addition, several yeast, mold, and pathogenic bacterial infections were cleared. The observations were made on the basis of symptoms such as sneezing, mucus secretion, color of the mucus, dizziness, fever, cold and cough.

The formulation given in Table 1 was arrived at by altering several variables such as amount of the probiotic blend, probiotic protecting ascorbic acid-sodium bicarbonate-sodium ascorbate, various amounts of natamycin, sodium propionate, glucose oxidase enzyme and polysorbate-60 (surfactant). Table 2 shows the amount of each ingredient after the dry composition (2.5 g) is dissolved in 260 ml of water, both in milligrams as well as in parts per million. Table 5 shows the strains of probiotics belonging to genera and species used in the specific multiple strain probiotic used in Formula-I of Table 1. These probiotic strains and their relative percentages have been arrived at after running several experiments and trials. I have also listed in Table 5, the therapeutic principles and specific bacteriocins and immunomodulins and volatile end products produced by each probiotic strain. These end products of growth of each probiotic strain and their functionality are highly specific and significantly different than other strains of probiotics used as components of the cumulative multiple strain probiotics. It was also discovered that liquified and then spray dried preparation of yeast and mold inhibitors and polysorbate using starch base (used as an ingredient in the formula) significantly and totally reduced the irritation in the nasopharyngeal cavity. Heat sensitive glucose oxidase enzyme has been applied onto the aforementioned spray dried preparation through accurate dosing using Acrison feeders or blenders.

The optimum amount of ascorbic acid for the maximum efficacy in combination with other ingredients has been determined after a series of trials. It was also observed that the entire composition went into solution instantly due to the acid base reaction of ascorbic acid and sodium bicarbonate. The combination buffer formed of ascorbic acid plus sodium bicarbonate, and the polysorbate-60, worked synergistically to accelerate the effect of probiotics and their therapeutic growth end products to inactivate the lipid enveloped coronavirus including influenza and corona RNA viruses. Due to the presence of antioxidant ascorbic acid in the formulation, it was serendipitously discovered that probiotic strains survived longer even in the dried formulation. It was also discovered that the above formulation allowed the administered nasal probiotics to stick to the mucosa to induce immunomodulation to eliminate the pathogenic viral, bacterial, as well as yeast and molds. In addition, lack of symptoms clearly proved that several allergens were flushed out of the nasopharyngeal cavity. It was of particular interest because this composition was significantly effective even when such a small dose of the active ingredients was included as opposed to massive doses, which induce nasal irritation and other unwanted side effects. The probiotic blend was also arrived at by taking into account the mucosal adhesion properties of the probiotics, in addition to their therapeutic physiological functions. During the COVID-19 pandemic, the people who have used this nasal irrigation did not contract any infection, as evidenced by lack of symptoms such as cough, high temperature, sore throat, fever, and respiratory distress. Furthermore they have maintained good levels of oxygen in their blood (between 90 to 100 percent). The oxygen was measured using pulse oximeter. Oxygen levels below 90 (specifically between 85 and 90) were considered suspicious of having COVID-19, during the pandemic period. Several, people in the age group of 60 and above also did not contract the infection. It distinctly proved that this nasal irrigation composition has significant inhibitory effect on the pathogenic nasal viruses, specially the COVID-19 coronavirus. This composition was tried on all age groups and genders ranging from 5 to 75 years. It is extremely surprising to note that the population of seventy and above, who are extremely susceptible to COVID-19 infections, did not pickup the infection during the corona pandemic period. The infection was evaluated on the basis of clinical symptoms.

No side effects were observed in any age group indicating that the composition has been synergistically buffered. Some people observed that their nasal passages cleared so well, and they have never felt so good before. CBD was included in the formulation to improve the efficacy of the composition, specifically to assist the probiotics and their immunomodulins. In several cases CBD significantly improved the nasal clearance. Surprisingly, it has exhibited superior synergy in improving the efficacy of the overall formulation. The CBD employed is a water-soluble hemp distillate having a potency of 15 mg/ml. In addition, tests evaluated the inclusion of cannabis oil (CBD and THC) as opposed to CBD only. Apparently, these cannabinoids enhanced the efficacy of the composition in protecting the nasopharyngeal cavities. In testing, cannabis derived CBD, cannabis oil with CBD and THC, and hemp derived CBD with THC were chosen and used in accordance with laws and regulations. Notably, even synthetic CBD, and CBD and THC combinations, can be used in these formulations. Also, the formulation of Example-I can also be applied as nasal spray.

The formula outlined in Example I also was effective when tried on dogs and cats. Here, rather than using the formula as a nasal irrigant, it was applied as a nasal spray. It is extremely important to treat domestic animals such as pets, since COVID-19 virus is zoonotic. The animals tested did not exhibit any signs of cough, sneezing etc. during the COVID pandemic period, indicating that the composition is suitable for intended pet application.

Example 2—To broaden the available methods of treating COVID-19 viral disease, the liquid preparation designed for nasal irrigation has been applied as a mouthwash and gargle. Roughly 10 to 20 ml of the nasal purge liquid was used to gargle for 30 to 55 seconds, touching the base of the tongue close to epiglottis. The results were phenomenal. It was important because COVID-19 disease, like any influenza virus, spreads through the mouth to gain entrance into the lungs. It was discovered that a combination of nasal irrigation as well as gargling with the composition outlined in Example 1 was excellent in controlling the pathogenic viral infection, as well as bacterial and yeast and mold infections. Several test subjects reported the combination worked excellently. As outlined in Example 1, the liquefied preparation was applied as mouth spray to dogs and cats with successful results. Both canines and felines responded well with no COVID-19 symptoms even after several months of observation. Again, it is noted that COVID-19, SARS-CoV-2 virus may infect domestic pets and animals since it is zoonotic. Eradicating this virus from household pets may contribute to protection of the human population from this pandemic or any future wave of the pandemic.

Example 3—All over the world, people have been instituting social distancing as a means to slow the transmission of COVID-19. Unfortunately, it is difficult to maintain such a measure forever, since numerous businesses are built upon group activity, filling capacity for a mass activity, or satisfying the fans need and desire to attend team events. Examples of businesses and events where social distancing is economically damaging include restaurants, travelling in airplanes, buses, and trains; attending sports stadiums for major team pastimes including football, soccer, cricket, basketball, and ice hockey; going to movie theaters and concerts; attending conferences, trade shows, and attending mass gatherings of many other types. An aspect of this invention is to provide the customers, fans, and attendees of group or mass-oriented business with an active defense against transmitted COVID-19. While some people may hope and trust that a vaccine will be an answer, vaccines present the problem that ultimately, they count on bodily defenses to defeat the virus. Unfortunately, bodily defenses are not reliable. If a potential victim has not had a vaccination, he is hopeless and helpless against the virus in his present situation. Even those who may have had vaccination are not reliably protected for very long, according to reports that human immunity to this virus lasts for only a short time. The invention is a remarkable improvement in protection because by itself it neutralizes or removes the virus from the potentially infected person, with no help or reliance on the human immune system. Further, the invention can be acquired and instantly applied with full effectiveness without delay and by anyone upon even spontaneous realization of the need. Thus, a person suddenly attending a mass event can protect himself nearly instantly.

An instantly useable extension of this invention is a nasal inhalant smelling salt with an ideal composition of liposomal probiotics and their bio-active nano peptides etc., and complementary herbal infusions which are very effective not only protecting probiotics but also in clearing the COVID-19 virus and other influenza viruses in the nasopharyngeal cavity, trachea, bronchi, bronchioles and the alveoli. An inhaling smelling salt of viricidal composition can destroy a coronavirus, especially the ones with a fat envelope, as in the case of wide spreading COVID-19 virus SARS-CoV-2. The composition of this viricidal smelling salt is presented in Table 3. The volatile compounds of the probiotic bacterial growth and their extracellular and intracellular therapeutic volatile principles in conjunction with the volatile herbal extracts, specially basil and clove exhibited antiviral effect through synergy when prepared using the composition in Table 3. We can hypothesize that viral inhibition exhibited by this composition is perhaps due to lysing of the lipid membrane of the coronavirus. The probiotic strains used and their relative percentages along with their description of end products of growth are presented in Table 6.

TABLE 3

Composition of a smelling salt with probiotics and their volatile growth end products to inactivate coronavirus SARS-CoV-2 and other influenza viruses

| Ingredient | Quantity (grams) | Typical range (grams) | Preferred range (grams) |
| --- | --- | --- | --- |
| Liposomal multiple strain probiotics blend along with their growth end products[1] | 1.0 | 0.1 to 1.5 | 0.25 to 1.25 |
| Alcohol infused basil and clove extract[2] | 2.2 | 0.5 to 4.0 | 0.75 to 3.0 |
| Cannabidiol (oil)[2] | 0.1 | 0.01 to 0.75 | 0.05 to 0,50 |
| Magnesium sulphate[3] | 2.0 | 1.0 to 4.0 | 1.5 to 2.5 |
| Sea salt[3] | 0.5 | 0.10 to 1.0 | 0.25 to 0.75 |
| 6% Sodium hypochlorite solution[4] | 0.2 | 0.1 to 0.5 | 0.15 to 0.35 |

[1]Principle active ingredient emitting volatiles
[2]Primary ingredient to further enhance volatile emissions produced by probiotics
[3]Salts to imbibe the volatile ingredients for gradual release with inhalation
[4]Agent to sterilize the imbibing salts prior to the addition of probiotics and herbal extracts The above specified formulation is made in small quantity using the following procedure: Weigh 2 grams of magnesium sulphate plus 0.5 grams of sea salt into a dish. Mix them together and add 0.2 grams of 6% sodium hypochlorite solution (12 mg of sodium hypochlorite) to sterilize the salt mix (to inactivate bacteria, mold spores, bacteria spores, and viruses). Mix the ingredients thoroughly and wait for few minutes. To the above mix add 2 grams (or 2 ml) of multi herb infused grain alcohol or commercially available Bio-Delight rum infused with additional herbs or Bio-Whiskey with natural botanicals. The following herbal extracts are included in the Bio-Whiskey: acacia, aloe, chirata, dill, artichoke, elecampane, gentian, guaran, rhatany root, serpentaria, valerian, veronica, turmeric, honey, cinchona, and wild cherry. The botanical names and therapeutic properties of these herbs are as previously outlined. As indicated earlier the concentration of cumulative herbs present in bio-whiskey did not exhibit any inhibitory effect on probiotic strains used.

Alternatively, such preparation can be made by infusing the herbs in grain alcohol. In another example 2 g or 2 ml of herbal extract infused Bio-Delight rum was used in the place of Bio-whiskey with similar results. However, Bio-Delight rum with herbal infusion was slightly superior to Bio-Whiskey in the novel inhaling smelling salt preparation, in terms of performance. The Bio-Delight rum had the following herbal infusions: acacia, artichoke, bay leaf, black berry, bryonia root, basil, alfalfa, calumba root, cinchona, clove, coriander, ginger, cinnamon, cumin, turmeric, and black pepper. In another example herbal extract infused Bio-Club vodka was used, which has the following herbal extracts: aloe, vanilla, and honey (infused in vodka). In my invention, in addition to the herbal extracts in the Bio-Delight rum, Bio-Whiskey, and Bio-Club vodka, concentrated extracts of basil, clove, and turmeric were added to the formulations. The concentrations of cumulative herbs present in the bio-Delight rum or bio-Club Vodka did not exhibit any inhibitory effect on probiotic strains used.

In another formula, in addition to the herbal infused alcohols and concentrated herbal extracts, liquid CBD was also added. CBD significantly improved the efficacy of the inhaling smelling salt. Yet, even without the addition of CBD, the formulation with Bio-Delight rum with 16 herbal extracts and additional highly concentrated basil, and clove performed well. If CBD is included in the formulation, the amount of the basil, and clove can be reduced significantly, yet with similar results. Apparently, CBD has synergistic effect with the probiotic produced volatile therapeutic compounds. Towards the end of preparation, the multiple strain probiotics along with their bio-active peptides and volatile therapeutic growth end products were add to the formula. The above prepared formulas were placed in a plastic or glass container with a tight closure or in a cartridge with screw type closure. Prior to inhalation, the cap is removed and, using one nostril at a time, it is inhaled deeply to reach the bottom of each and every alveoli of the lung. Conversely, the composition can also be applied using a standard nebulizer with proper liquefaction of the ingredients using a suitable solvent such as water.

The preparation was tried on patients of all age groups and genders ranging from 5 years to 75 years. They were asked to inhale once in the morning and once in the evening if they are at home or office. If they have to go to public places or a crowded place, they were asked to inhale before and after visiting the place. For example, in a restaurant or ballpark a person can inhale prior to going into the place and after leaving the place. Assuming the person stays at such place for 3 or 4 hours, inhaling at the beginning and ending of the 3 or 4 hours will do the job.

As a practical illustration, this preparation was also given to a patient who was tested positive for COVID-19. During a subsequent lockdown period due to the COVID-19 positive test, the patient was asked to smell twice in a day. The patient did not develop any COVID-19 distress symptoms in the 14 days quarantine. Furthermore, the test (PCR test) at the end of 14 days came out negative for COVID-19. Similar results were found with other subjects. The subjects who did not have COVID-19 symptoms did not develop COVID-19 disease at all when using this smelling salt, indicating that it is viricidal to the SARS-CoV-2 virus causing COVID-19 disease.

In addition to the ingredients listed in Table 3, further testing evaluated the addition of a minimal amount of ammonium carbonate. In another composition, sodium hypochlorite has been replaced by a minimal quantity of liquid chloroform. Both 0.25 grams of ammonium carbonate and 0.2 ml of chloroform were included in the formula outlined in Table 3 and tested. Although ammonium carbonate in the form of inhaling smelling salt is not generally approved, in one of the formulas 0.2 grams (0.1 to 0.4 grams range) was included along with the ingredients outlined in Table 3, on an experimental basis only. In addition, 0.2 ml of liquid chloroform (0.1 to 0.5 ml range) was added in the place of sodium hypochlorite to inactivate bacteria, yeast and molds, present as contaminants in the salts of the mixture, which is placed in a closed cartridge. Although they are only experimental, most of these inclusions were very effective in retarding the viral, bacterial, yeast and mold infections, including coronavirus, specifically SARS-CoV-2, in conjunction with the volatile end products of multiple probiotic bacteria.

A proposed mechanism of action is that the significantly small amount of ammonium carbonate along with the magnesium sulfate and sea salt in the presence of the synergistic probiotic and herbal mixture has activated lung tissue's inhalation response and has inactivated the coronavirus and other pathogenic microorganisms. Thus, the above ingredients are included in the current formulation in countries where such ingredients are legal to include as part of the nasal inhalant. The uniqueness of this invention is such in that there is a significant synergy of the ingredients to inactivate the RNA viruses including corona virus, SARS-CoV-2, which causes COVID-19 disease.

For use with domestic pets, the above prepared inhaling salt is placed in a porous container and placed in the vicinity of the animal's shelter for the animal to smell occasionally, to ward off the viral infections. The formula appears to be effective for pets also, which is determined on the basis of clinical symptoms such as cough, significant nasal discharge, temperature, and difficulty in breathing etc. This preparation did not exhibit any side effects either in humans or in animals, showing safety, which is not always present in other nasal inhalants.

Example 4—This example and Table 4 show a novel composition of an antioxidant liposome for treating a coronavirus. The composition contains multiple strains of probiotics along with their growth end products such as bioactive therapeutic peptides, bacteriocins and immunomodulins, and ascorbic acid, sodium bicarbonate, sodium ascorbate and lecithin. To further assist the probiotics, the composition also includes basil, clove, and turmeric concentrate, and optionally CBD. The resulting liposome can curtail a COVID-19 infection and is effective against other coronaviruses including influenza virus, secondary pathogenic bacterial infections, and yeast and mold infection.

TABLE 4

Composition of probiotics liposome to curtail or assist fast recovery from COVID-19, SARS-CoV-2 coronavirus, and other influenza virus infections.

| Ingredient | Quantity (grams) | Typical range (grams) | Preferred range (grams) |
| --- | --- | --- | --- |
| Multiple probiotics strain blend along with their growth end products[1] | 5.0 | 0.50 to 6.0 | 1.0 to 5.5 |
| Ascorbic acid[2] | 20 | 10 to 30 | 15 to 25 |
| Sodium bicarbonate[2] | 7.5 | 2.5 to 12 | 4 to 9 |
| Sodium ascorbate[2] | 2.0 | 1.0 to 5.0 | 0.5 to 4.0 |
| Conc. basil extract[3] | 0.5 | 0.1 to 1.0 | 0.25 to 0.75 |
| Conc. turmeric extract[3] | 0.5 | 0.1 to 1.0 | 0.25 to 0.75 |
| Conc. clove extract[3] | 0.5 | 0.1 to 1.0 | 0.25 to 0.75 |
| Cannabidoil (CBD)[3] | 0,5 | 0.1 to 2.0 | 0.2 to 1.5 |
| Lecithin[4] | 30.0 | 15 to 40 | 20 to 35 |

[1]Principle active ingredient
[2]Primary probiotics protecting antioxidants
[3]Secondary probiotics stimulants
[4]Liposome main ingredient to make liposome of the rest of the ingredients in the formula The details of the herbal extracts and CBD outlined in Example-4 (Table 4) are presented below.

Turmeric (dietary supplement and herbal supplement) botanical name *Curcuma longa*, herb strength, 1:1.5, each 1 ml has 666 mg of turmeric compound weight equivalent, other ingredients present are grain alcohol 58 to 68% by volume, and deionized water, and it is 100% gluten free. Recommended dose: 3 ml per day mixed in water or juice (2000 mg of active turmeric compound/day).

Holy basil (dietary supplement and herbal supplement) botanical name *Osmium sanctum*, herb ratio 1:2 strength, each ml has 500 mg herb weight equivalence. Other ingredients present are grain alcohol (45-55%) by volume, and deionized water, 100% gluten free. The recommend dose is 3 ml per day mixed in water or juice (1500 mg active compound/day).

Clove oil (100% pure), botanical name *Eugenia caryophyllata*. Highly concentrated natural oil obtained by steam distilling buds of cloves.

Water soluble hemp distillate, potency 15 mg/ml. If there is restriction in use of CBD (due to local or federal governmental regulations), it can be replaced by raising the concentrations of the basil and turmeric extracts accordingly.

The above composition presented in Table 4 was prepared using the following procedure: weigh and dispense 20 grams of ascorbic acid in a beaker and add one half cup of water (118 ml or grams). After the powdered ascorbic acid is completely dissolved, add 7.5 grams of sodium bicarbonate powder, gradually with stirring to eliminate spilling due to the reaction. After the completion of reaction add additionally 2.0 grams of sodium ascorbate. Weigh separately 30 grams of dried lecithin granules or liquid lecithin and add to one cup of water (236 ml or grams). Blend the lecithin and water in a Waring blender for 1 to 2 minutes at medium or high speed. Then add the ascorbic acid-sodium bicarbonate-sodium ascorbate liquid (118 ml or grams) to the liquified lecithin in the blender and blend for one or two more minutes. At this stage add multiple probiotics with their immunomodulins, along with 0.5 grams of each of concentrated basil extract, concentrated clove extract, and concentrated turmeric extract. Optionally, add 0.25 ml or grams of water-soluble CBD extract to the above blend and mix the entire composition for an additional 1 to 2 minutes. Optionally, add either water soluble or oil soluble vitamins and other antioxidants such as glutathione, alpha lipoic acid, and finally ground aspirin, available over the counter, or paracetamol to the blend before sonication. The liposomal aspirin or paracetamol will not only reduce fever but also act to thin the blood during COVID-19 infection, to prevent blood clots in blood vessels as an attempt to assist the therapeutic effect of probiotics and other probiotic protecting antioxidants.

Then add the blended mix into a sonicator and sonicate with gentle stirring for about 16 minutes, with typical times ranging from 10 to 20 minutes, and longer times being acceptable. At the stage liposome should not have any visible precipitate. Dispense the prepared liposome into a clean container and store in a refrigerator. It is also acceptable to freeze, dry, or freeze dry or spray dry the liposome to produce a powder having a longer shelf life and be convenient for long-term storage and shipping. The individual probiotics strains included in the Formula-4, along with their relative percentages and their defined therapeutic growth end products are presented in Table-7.

Recommended daily dosages for the above prepared liquid antioxidant liposome are one dose of 1 ounce or two doses of one-half ounce each. This preparation was given to several test subjects of all ages who were monitored for coronavirus infection over a period of 5.5 months during the coronavirus pandemic period (February through middle of August 2020). Surprisingly, the results were as good as could be hoped for in that no test subject got sick due to coronavirus. In addition, the above preparation was given to a patient who had been infected with COVID-19. This patient recovered quickly, within one to two weeks.

TABLE 5

Probiotic components, in terms of individual strains (percentage in total), and their growth end products included as multiple probiotic blend in formula-I, as presented in Table 1.

| Probiotic strain identification | % of particular pro-biotic strain in the mix probiotic blend | Identification of growth end products including bacteriocins |
|---|---|---|
| Lactococcus lactis subsp. lactis | 25 | Biopeptides, Nisin, Volatile organic acids |
| Lactococcus lactis subsp. cremoris | 15 | Biopeptides, Diplococin, Organic acids |
| Lactococcus lactis subsp. lactis var diacetylactis | 10 | Diacetyl, Acetyl Methyl carbinal, Biopeptides |
| Streptococcus thermophilus | 10 | Biopeptides, Thermophilin, Volatile organic acids |
| Lactobacillus sporogenes | 17.5 | Volatile organic acids, Bio- active peptides |
| Lactobacillus bulgaricus | 9.34 | Bulcaricin, Bio-active peptides, Volatile organic acids |
| Lactobacillus acidophilus | 13.16 | Acidophilin, Bio-active peptides, Organic acids |

TABLE 6

Probiotic strains and their relative percentages in the multiple probiotic blend along with their growth end products (immunomodulins) used as a component in Example 3 of Table 3.

| Probiotic strain identification | % of particular probiotic strain in the mix probiotic blend | Identification of growth end products including bacteriocins of each strain |
|---|---|---|
| Propionibacterium sherinanii | 50 | Propionicin, Propionic acid, Bio-active peptides, Butyric acid, Acetic acid |
| Lactococcus lactis subsp. lactis | 20 | Bio-active peptides, Volatile carbonyls, Lactic acid and other Volatiles, Nisin |
| Lactobacillus sporogenes | 10 | Volatile organic acids, Bio- active peptides |
| Lactococcus lactis subsp. lactis var diacetylatis | 15 | Acethyl methyl carbinol, Diacetyl, Lactic acid, Nisin-Z |
| Pediococcus acidolactici | 5 | Volatile organic acids, Pediocin |

TABLE 7

Probiotic component strains and their relative percentages in the multiple probiotic blend along with their growth end products (immunomodulins) used as a component in Example 4 of Table 4.

| Strain identification | Percentage in the probiotic blend | Growth end products present in the blend |
|---|---|---|
| Lactobacillus acidophilus | 10 | Acidophilin, Lactic acid, Volatile acids, Nano bio-active peptide |
| Lactobacillus sporogenes | 20 | Organic volatile acids, Bio-active nano peptides |
| Propionibacterium arabinosum | 10 | Jensinin, Propionic acid, Butyric acid, Acetic acid |
| Propinibacterium shermanii | 10 | Propionicin, Propionic acid, Butyric acid, Acetic acid |
| Streptococcus thermophilus | 15 | Thermophilin, Bio-peptides, Volatile organic acids |
| Lactobacillus casei | 15 | Bio-peptides, Volatile organic acids |
| Saccharomyces boulardi | 7.5 | Peptides and Volatile bio-compounds |
| Bifidobacterium bifidum | 12.5 | Bifidocin, Lactic acid, Bio-active peptides |

The liposome also was evaluated with variations of ingredients to identify which appeared to provide the better effectiveness. The standard for comparison had the liposome prepared with, herbal extracts, CBD, ascorbic acid, sodium bicarbonate, and sodium ascorbate. However, the probiotics were not included. A first test version had the liposome prepared with ascorbic acid and herbal extracts only, without sodium ascorbate, sodium bicarbonate, CBD, and probiotics. A second test version had the liposome prepared with concentrated herbal extracts of clove, turmeric, and basil in combination with ascorbic acid and sodium ascorbate along with multiple probiotics strain, but without inclusion of their all other immunomodulins and growth end products. A third test version had the liposome prepared with CBD in combination with the herbal extracts (clove, turmeric and basil), ascorbic acid, sodium bicarbonate, sodium ascorbate, along with multiple strain probiotics including their growth end products (bio-active peptides, organic acids, bacteriocins and other immunomodulins).

The results showed that this first test version of the liposome did not improve the symptoms of COVID-19 patients. The standard version performed slightly better than the first test version liposome. The second test version performed significantly better than the standard liposome. This second test version was better than the first test version and standard. The third test version, which showed the best effectiveness compared to second test version in curtailing COVID-19, proving it to be the best out of all versions. When CBD was not used, an elevated concentration of the herbal extracts in the liposome acted as a substitute. Distinctly the discovery proved that there is a synergy between probiotics and their growth end products, herbal extracts and ascorbic acid, sodium ascorbate in lecithin liposome, and also synergy was observed between herbal extracts and CBD. Even the smallest amount of CBD exhibited excellent properties in conjunction with the multiple strain probiotics along with their growth end products including therapeutic bio-peptides, bacteriocins and immunomodulins, antioxidant herbal extracts, ascorbic acid, sodium bicarbonate and sodium ascorbate in liposome to prevent or cure the COVID-19 infection due to SARS-CoV-2 virus during the pandemic period in the months of February through August of 2020. It was clearly proven that the end products of growth of multiple probiotics along with their probiotics and probiotic protectant antioxidants had significant effect on retardation of COVID-19. The above composition (third test version) also prevented people from getting sick from other influenza viruses, bacteria, yeast, and mold infections (observed by clinical symptoms). Excellent protection and stimulatory effect of probiotics was observed with the concentration of ascorbic acid, sodium bicarbonate, and sodium ascorbate used in the formulations listed in Table 1 and Table 4 of this embodiment. The combination of selected herbs (basil, clove, and turmeric), the ascorbic acid-sodium bicarbonate-sodium ascorbate, surfactant polysorbate, and CBD significantly improved the protective effect and viability of multiple strain probiotics when transformed into liposome. The composition of which is presented in table-4 of this embodiment. Although the antioxidants (herbs, ascorbic acid and its salts, and CBD) and stimulants (polysorbate) are primarily used in the formula to protect viability of strains of probiotics, it was later discovered that they have exhibited synergistic effect not only to enhance the protection of probiotics but also to significantly improve the long lasting antioxidant effect in vivo, in combination with the growth end products of multiple strain probiotics, such as bio-peptides, bacteriocins, organic acids and other immuno-modulins. Thus the combination of these ingredients, although intended for some other function, was proven extremely successful not only to prevent but also to treat coronaviral infections.

A tentative explanation for performance of the best performing liposomes is that their active elements stayed longer in the blood and suppressed the COVID-19 infection by improving the resistance of the nasopharyngeal orifices, tracheas columnar epithelial cells, bronchi and bronchiole tissue, and the alveolar tissue, including both the surfactant producing type-2 pneumocytes and type-1 pneumocytes. The curative property of the above preparations may be due to immunomodulatory effects of probiotics and their immunomodulins, included in the novel liposome by stimulating the production of T-reg cells and interleukin-10 by the lymphatic system to suppress the overactive immune system in the COVID-19 patients due to cytokine storm. In addition, the specified probiotics included in this antioxidant liposome must have stimulated production of definsins by the epithelial cells of the respiratory tract to ward off the COVID-19 viral infection. The addition of the probiotic blend along with its immunomodulins significantly improved the efficacy of this antioxidant blend. It either prevented or assisted in curing the COVID-19 infection, as shown by success when compared to the probiotic blend without its own growth end products (immunomodulins). This is part of the superiority of this invention. It can be hypothesized that the multiple mixed strain probiotics and their immunomodulins of this invention might have also synergistically suppressed the SARS-CoV-2 coronavirus adhesion to ACE-2 receptors, in addition to modulating the immune system to inactivate the virus and its pathological effects. Perhaps it could also be due to their bio-active therapeutic peptides present in the growth medium (which were also made into liposomes), might have inhibited the angiotensin converting enzyme and thus might have reduced the concentration and production of Angiotensin-II, which is responsible for the inflammation and oxidation of blood vessels causing hypertension and other disorders such as blood clots etc. Thus, even though COVID-19 virus attached and inactivates ACE-2 receptors in blood vessels, the therapeutic liposomal bio-peptides of the probiotics might have circumvented the problem by reducing the production of Angiotensin-II. In addition, the antioxidants (primary used in liposomes to protect the probiotics) perhaps synergistically must have improved the above reaction, to protect the patients with advanced COVID-19 infections. This preparation was also given to household pets where it apparently eliminated zoonotic viral transfer, determined on the basis of lack of COVID-19 symptoms. It was administered by adding to the pet's water or food, in a dose adjusted according to their body weight in relation to human dosage. The efficacy of the administered preparation in pets was judged solely on the basis of symptoms.

Some of these additional serendipitous observations were made while running the clinical trials outlined in Example 4.

Patient-A: 65-year-old female had a comorbid disease condition of hypertension. The blood pressure readings were around 190/105 systolic/diastolic, prior to the treatment. She was put on a blood pressure reducing medication by her physician at a dosage rate of two tablets per day. The medication prescribed had the following pharmaceutical ingredients, Telmisartan and Amlodipine. Each tablet contained pharmaceutical ingredients, Telemisartan IP-40 mg and Amlodipine Besylate IP, equivalent to Amlodipine-5 mg. Although, physician recommended taking two tablets/day to reduce the blood pressure (BP), she was able to reduce BP by only up to 165/102, even after taking medication for sufficient length of time. Surprisingly, the diastolic pressure did not go below 100, even after continuously taking medication. Besides, the subject had severe side effects such as slight dizziness and headache. She has reduced the dosage from 2 tablets/day to ½ tablet per day. The daily dose reduction from two tablets (Telemisartan IP-80 mg and Amlodipine-10 mg) to ½ table had only Telemisartain IP-20 mg and Amlodipine-2.5 mg, was to reduce the undesirable side effects. The BP readings at this dosage level were 175/105. She was not able to reduce the systolic as well as diastolic blood pressure beyond these numbers with the above specified prescription medicine, more specifically the diastolic blood pressure, which is the most dangerous one out of the two in terms of cardiac health. At this stage she was categorized as patient with chronic high blood pressure or hypertension. When the COVID-19 infection started in November 2019 in China, and when it was declared as pandemic in March 2020, the subject was very particular about her hypertension being a comorbid condition with a possibility of picking up COVID-19 lethal infection.

At this stage, she started to take the lecithin coated liposome product identified previously in Example-4 as the third test version, with a composition of combined multiple strain probiotics along with their growth end products, ascorbic acid, sodium ascorbate, sodium bicarbonate, turmeric, clove, basil extracts and CBD. This was given as a preventative measure to protect her from COVID-19 because of her comorbid condition of high systolic/diastolic blood pressure. She has continued to take only ½ tablet of the earlier specified BP medication. As a total surprise, her BP dropped to 152/98 after one week, and two weeks later it dropped to 143/75. After one and half months, it dropped down to 135/72. This was a total surprise, in particular because the diastolic blood pressure dropped into the 70 to 75 range, which is extremely favorable.

A key chemical process in blood pressure control is conversion effect of ACE-2 to produce Angiotensin-1,7 (AT-1,7), according to either a high level or a low level of Angiotensin II (AT-II). AT-1,7 is a key vasodilator to control normal blood pressure. Such a significant drop in blood pressure through homeostasis, reasonably indicates that the liposome product successfully allowed and possibly even enhanced conversion of AT-II to AT-1,7 in the low-level route. SARS-CoV-2 can bind with ACE-2 receptors and thereby disrupt conversion to AT-1,7 in the high-level route. This vast drop in blood pressure to normal range again shows important support for conversion of AT-II to AT-1,7, possibly also in the high-level route of AT-II, where SARS-CoV-2 can interfere. Thus, the trial not only suggests that the liposome supports the mechanism enabling lowering of the blood pressure, but it also suggests that an infected patient with chronic comorbid hypertension may be significantly protected from a negative outcome due to the comorbid hypertension.

The favorable result with respect to lowered blood pressure establishes an interaction between the operation of the liposome and the operation of the agents of Examples 1-3. When these agents inactivate coronavirus near entrance to the respiratory passages as suggested in FIGS. 1-3, those coronaviruses never have a chance to bind with ACE-2 receptors. As a result, more ACE-2 receptors are available at the inlets of the respiratory passages to carry on their normal physiological functions. To this extent, more ACE-2 receptors will be available in blood vessels without the virus degrading ACE-2 availability. Hence, the nasal treatment to inactivate COVID-19 virus is an adjunct to the operation of the liposome.

The patient continued taking the liposome orally, started using the nasal irrigation product of Example 1 twice a week and employed the gargle of Example 2. To eliminate the future infection due to COVID-19 the patient has also regularly inhaled the smelling salt of Example 3. This patient's experience shows numerous beneficial results of employing the product set of Examples 1-4. Despite a comorbid condition, the patent did not contract the COVID-19 disease. In addition to avoiding the COVID-19 infection, the patent also experienced a profound reduction in blood pressure. While the composition was not designed for treatment of blood pressure, this resulting lowering of blood pressure shows a successful treatment of an underlying cause of high blood pressure to a degree not often encountered, Patient B: 75-year-old male has a high blood sugar level of 450 mg/dl three hours after meal, and a 275 mg/dl after fasting overnight. The patient was put on following blood sugar medication prescribed by his physician: The initial recommended pharmaceutical therapeutic dose by physician was Gliclazide IP-160 mg and Metformin Hydrochloride IP-1000 mg/day. However, due to severe gastric irritation and severe constipation, the subject took only ⅓rd of the table/day, which amounts to pharmaceutical ingredients Gliclazide IP-26.4 mg and 165 mg Metformin Hydrochloride. The patient has developed severe gastric irritation and constipation, and thus could not continue the above prescribed dose of medication. He has cut it down ⅓ dose because of severe gastritis. His blood sugar levels were still 165 mg/dl after fasting, and 290 mg/dl 3 hours after meals, indicating that he was an established diabetic patient. During the COVID-19 pandemic, due to his age, he started to take the liposome preparation outlined in Example 4, possibly to prevent COVID-19 infection. Yet, he continued to take ⅓ dose of the prescribe medication. After 4 to 6 weeks of the above treatment schedule, his blood sugar dropped to 116 mg/dl after fasting and 145 mg/dl, three hours after the meal. Despite this comorbid condition, he did not display any symptom of COVID-19 infection, and, in addition, his blood sugar level improved. He was treated with the liposome product identified previously in Table-4, as the third test version of combined multiple probiotics along with their growth end products, ascorbic acid, sodium ascorbate, sodium bicarbonate, turmeric, clove, basil extracts and CBD (with lecithin as a liposomal coating agent). Blood sugar continued to be low despite elimination of CBD from the formula. The patient showed no symptom of COVID-19 infection. However, the patient reported that the presence of CBD in the formulation produced a superior feeling of good overall, in terms of physical condition indicating CBD has significant influence in the formula.

Similar results were obtained using powdered liposome in place of liquid liposome outlined in Example 4. The significant reduction of blood sugar following use of this invention is a serendipitous observation. While the composition was not designed for treatment of blood sugar level, this resulting lowering of blood sugar level shows a successful treatment of an underlying cause of high blood sugar. Although the liposome is given mainly to prevent or control the COVID-19 infections, surprisingly as a serendipitous observation, the blood sugar also got reduced (of course with limited and small dosage of medication). Thus, my invention is of significant importance, in that it not only reduced the COVID-19 infection but also significantly reduced the comorbid disease of high blood sugar.

Example-5. The successful experimental trials conducted using the compositions outlined in Example 1, 2, 3 and 4 of this discovery, has been combined and tested on several subjects involving all age groups and sexes, in this Example 5. The experimental methodology involved using nasal irrigation as disclosed in Example 1, mouthwash and gargling as disclosed in Example 2, inhaling the smelling salt twice a day as disclosed in Example 3, and finally, taking orally twice a day (½ ounce in the morning and ½ ounce in the evening) or once a day using one ounce of the probiotic liposome as disclosed in Example 4. All participants took part during the pandemic period of COVID-19, showed no new occurrences of COVID-19 infection, as well as assisting to cure the COVID-19 positive victims. It is of significance in that, since there is no successful treatment so far to prevent or cure the lethal COVID-19 coronaviral infection due to SARS-CoV-2 virus in the world. Particularly with respect to older patients who are prone to have cardiovascular problems due to age, it is notable that none suffered thrombosis during the trial.

Currently government and medical authorities have only minimal recommendations to protect the public from transmission of COVID-19 disease. These are to wear facemasks and maintain a person-to-person social distancing variously set at six to twelve feet. These measures are impractical if not impossible to sustain on a full-time basis. The compositions and treatments disclosed herein provide alternative, selectively self-administered solutions to the danger of COVID-19 disease. Using either all or some fractions of the disclosed compositions and methods, people can engage in traditionally practiced events and lifestyles without the undue restraint of practicing social distancing.

The nasal composition inhalation is one of the best approaches to prevent or eliminate the coronavirus entry or multiplication in the human respiratory tract. In addition, inactivated and lysed coronavirus particles remaining in a person who has been treated with the present compositions may provide protection from further infection. The particles may serve as a shortcut to enhanced natural immunity in humans by serving as a source of attenuated virus segments supplied to the immune system, thus providing vaccine-like protection to them from this disease. These compositions also may protect people from getting influenza virus, which kills vast numbers of people around the world. In another aspect, these products are economical and can be afforded by people at any economic level and at less cost than any other presently proposed treatment. While currently there is no applicable vaccine, even if a vaccine is discovered at a later date, these compositions are not dependent upon specific configurations of the virus and will remain valuable against mutations of the coronavirus and thus can be used also in conjunction with vaccines. Thus, they are effective in situations where protection from a mutation or spot protection is needed.

In still another aspect of protection, these compositions offer hands-on administration at each person's convenience of time and place and does not create a social barrier like wearing face mask or standing at distance from everyone else. Human beings employ all forms of communication, including facial expression and physical closeness, to develop friendship, romance, and even confident business relationships. Personal relationships and economic development will benefit when virus control in the form of masks and distancing no longer are needed as the minute-by-minute fabric of daily conduct. It can be reasonably expected that economies will be brought back into line with eliminate of scare, impractical social distancing, and wearing uncomfortable N-95 or other nose masks which look unappealing, uncomfortable, and highly unproductive to perform daily duties at work place and at home. This invention will put our lives back to normal since human beings are social beings and may suffer depression if required to live in isolation.

The foregoing is considered as illustration only of the principle of the invention, further since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow:

What is claimed is:

1. A method of treating SARS-CoV-2 coronavirus infection by administering to a human subject in need thereof an effective amount of a preparation of:
    a combination of viable probiotics comprising *Lactococcus lactis* subsp. *lactis, Lactobacillus sporogenes, Streptococcus thermophilus*; and
    immunomodulins of said viable probiotics.

2. The method of claim 1, wherein said preparation further comprises an herbal extract that is a stimulant of said viable protiotics.

3. The method of claim 2, wherein said herbal extract is a combination of clove, turmeric, and basil.

4. The method of claim 1, wherein said preparation is administered by a sinus flush.

5. The method of claim 1, wherein said preparation is administered by smelling salt, and the smelling salt comprises sodium hypochlorite solution.

6. The method of claim 5, wherein said smelling salt further comprises cannabidiol.

7. The method of claim 5, wherein said smelling salt further comprises ammonium carbonate.

8. The method of claim 5, wherein said smelling salt further comprises chloroform.

9. A method of treating SARS-CoV-2 coronavirus infection by administering to a subject in need thereof, said subject chosen among human, dog, or cat, an effective amount of a preparation comprising:
    a liposome of a viable probiotic, wherein the said viable probiotic is a combination of *Lactococcus lactis* subsp. *lactis, Lactobacillus sporogenes*, and *Streptococcus thermophilus*, and immunomodulins of said viable probiotic.

10. The method of claim 9, wherein said preparation further comprises:
    protectants and stimulants of said viable probiotic and of said immunomodulins.

11. The method of claim 9, wherein said preparation further comprises:
    an herbal extract that is a stimulant of said viable probiotic.

12. The method of claim 11, wherein said herbal extract further comprises stimulants of said viable probiotic and of said immunomodulins within said liposome, said stimulants comprising:
    a combination of clove, turmeric, and basil.

13. The method of claim 9, wherein said preparation further comprises protectants of said viable probiotic and of said immunomodulins within said liposome, said protectants comprising:
    polysorbate;
    natamycin;
    sodium propionate;
    and glucose oxidase.

14. The method of claim 9, wherein said preparation further comprises buffering agents of said viable probiotic and of said immunomodulins within said liposome, said buffering agents comprising:
    ascorbic acid;
    sodium bicarbonate;
    sodium ascorbate;
    and sodium chloride.

15. The method of claim 10, wherein:
said preparation is administered by a sinus flush.
16. The method of claim 1, wherein said preparation further comprises:
protectants and stimulants of said probiotics and said immunomodulins.

* * * * *